United States Patent
Crews et al.

(10) Patent No.: US 9,456,825 B2
(45) Date of Patent: Oct. 4, 2016

(54) ENDOSCOPIC IMPLANT SYSTEM AND METHOD

(71) Applicant: Boston Scientific Scimed, Inc., Maple Grove, MN (US)

(72) Inventors: Samuel Crews, Woodside, CA (US); Bretton Swope, San Francisco, CA (US); Justen England, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 436 days.

(21) Appl. No.: 13/764,707

(22) Filed: Feb. 11, 2013

(65) Prior Publication Data

US 2013/0304094 A1 Nov. 14, 2013

Related U.S. Application Data

(62) Division of application No. 12/175,242, filed on Jul. 17, 2008, now abandoned.

(60) Provisional application No. 60/950,584, filed on Jul. 18, 2007, provisional application No. 61/042,862, filed on Apr. 7, 2008.

(51) Int. Cl.
*A61F 5/00* (2006.01)
*A61B 17/128* (2006.01)
(Continued)

(52) U.S. Cl.
CPC ......... *A61B 17/128* (2013.01); *A61B 17/0643* (2013.01); *A61B 17/0644* (2013.01);
(Continued)

(58) Field of Classification Search
CPC .......... A61B 17/0401; A61B 17/1114; A61B 17/0469; A61B 17/11; A61B 2017/0403; A61B 2017/0404; A61B 2017/0406; A61B 2017/0408; A61B 2017/0409; A61B 2017/0417; A61B 2017/0419; A61B 2017/042; A61B 2017/0438; A61B 2017/0445; A61B 2017/00827; A61B 2017/00269; A61B 2017/00278; A61B 2017/3488; A61F 5/0083; A61F 5/0086; A61F 5/0003
USPC .......... 606/151, 153, 139, 142, 167; 600/37
See application file for complete search history.

(56) References Cited

U.S. PATENT DOCUMENTS

| 3,663,965 A | 5/1972 | Lee et al. |
| 4,134,405 A | 1/1979 | Smit |

(Continued)

FOREIGN PATENT DOCUMENTS

| CH | 680263 | 7/1992 |
| DE | 8708978 | 11/1987 |

(Continued)

OTHER PUBLICATIONS

International Search Report from PCT Patent Application No. PCT/US2002/027177 mailed Feb. 14, 2003.
(Continued)

*Primary Examiner* — Dianne Dornbusch
(74) *Attorney, Agent, or Firm* — Bookoff McAndrews, PLLC

(57) ABSTRACT

Disclosed is a system for endoscopically implanting a medical implant, including an anchor, within a body cavity such as adjacent the gastroesophageal junction in a human stomach. The system includes one or more anchors positionable within one or more openings formed in tissue within the body cavity, such as cutouts formed in plicated body tissue. Tools are disclosed for positioning the anchors within the openings, and for coupling a food restrictor to the anchors.

20 Claims, 26 Drawing Sheets

(51) Int. Cl.
*A61B 17/064* (2006.01)
*A61B 17/00* (2006.01)

(52) U.S. Cl.
CPC .............. *A61B2017/00862* (2013.01); *A61B 2017/0647* (2013.01); *A61F 5/0003* (2013.01); *A61F 5/0083* (2013.01); *A61F 5/0086* (2013.01)

(56) References Cited

U.S. PATENT DOCUMENTS

| | | |
|---|---|---|
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 1,408,865 A | 3/1992 | Cowell |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schenck |
| 5,514,176 A | 5/1996 | Bosley |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Elias |
| 5,887,594 A | 3/1999 | LoCicero, III |
| 5,897,562 A | 4/1999 | Bolanos et al. |
| 5,910,144 A | 6/1999 | Hayashi |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egres |
| 6,051,015 A | 4/2000 | Maahs |
| 6,086,600 A * | 7/2000 | Kortenbach .................. 606/139 |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman |
| 6,416,522 B1 | 7/2002 | Strecker |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor et al. |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,692,507 B2 * | 2/2004 | Pugsley et al. .............. 606/153 |
| 6,733,512 B2 | 5/2004 | McGhan |
| 6,736,828 B1 * | 5/2004 | Adams et al. ................ 606/213 |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |

(56) References Cited

U.S. PATENT DOCUMENTS

| | | |
|---|---|---|
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,056,305 B2 | 6/2006 | Garza |
| 7,066,945 B2 | 6/2006 | Hashiba et al. |
| 7,074,229 B2 | 7/2006 | Adams et al. |
| 7,083,629 B2 | 8/2006 | Weller et al. |
| 7,083,636 B2 * | 8/2006 | Kortenbach .................. 606/220 |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,160,312 B2 | 1/2007 | Saadat et al. |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,571,729 B2 | 8/2009 | Saadat et al. |
| 7,699,863 B2 | 4/2010 | Marco et al. |
| 7,744,627 B2 | 6/2010 | Orban, III |
| 7,753,870 B2 | 7/2010 | Demarais et al. |
| 7,766,861 B2 | 8/2010 | Levine et al. |
| 7,837,669 B2 | 11/2010 | Dann et al. |
| 7,931,661 B2 | 4/2011 | Saadat et al. |
| 8,020,741 B2 | 9/2011 | Cole et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 * | 6/2002 | Schurr et al. .................. 606/151 |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065340 A1 * | 4/2003 | Geitz .......................... 606/151 |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0120289 A1 | 6/2003 | McGuckin, Jr. et al. |
| 2003/0158569 A1 | 8/2003 | Wazne |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220657 A1 * | 11/2003 | Adams .......................... 606/139 |
| 2003/0220660 A1 * | 11/2003 | Kortenbach et al. .......... 606/151 |
| 2003/0236536 A1 * | 12/2003 | Grigoryants et al. ......... 606/151 |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 * | 3/2004 | DeVries ............... A61B 17/064 606/213 |
| 2004/0059289 A1 | 3/2004 | Garza et al. |
| 2004/0068276 A1 | 4/2004 | Golden et al. |
| 2004/0082963 A1 | 4/2004 | Gannoe et al. |
| 2004/0088023 A1 | 5/2004 | Imran et al. |
| 2004/0092892 A1 * | 5/2004 | Kagan et al. .................. 604/264 |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0116949 A1 * | 6/2004 | Ewers et al. .................. 606/167 |
| 2004/0117031 A1 | 6/2004 | Stack et al. |
| 2004/0122456 A1 * | 6/2004 | Saadat et al. .................. 606/157 |
| 2004/0138761 A1 * | 7/2004 | Stack et al. .................. 623/23.65 |
| 2004/0139761 A1 | 7/2004 | Stack et al. |
| 2004/0143342 A1 * | 7/2004 | Stack et al. .................. 623/23.65 |
| 2004/0148034 A1 | 7/2004 | Kagan et al. |
| 2004/0153167 A1 | 8/2004 | Stack et al. |
| 2004/0158331 A1 * | 8/2004 | Stack et al. .................. 623/23.65 |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 * | 11/2004 | Levine et al. .............. 623/23.65 |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0249367 A1 * | 12/2004 | Saadat et al. ...................... 606/1 |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 * | 3/2005 | Dann et al. .................. 623/23.65 |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 * | 5/2005 | Stack et al. .................. 606/151 |
| 2005/0096750 A1 | 5/2005 | Kagan et al. |
| 2005/0119671 A1 | 6/2005 | Reydel et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0203550 A1 * | 9/2005 | Laufer et al. .................. 606/151 |
| 2005/0216040 A1 | 9/2005 | Gertner et al. |
| 2005/0216042 A1 | 9/2005 | Gertner |

(56) References Cited

U.S. PATENT DOCUMENTS

| | | |
|---|---|---|
| 2005/0228504 A1 | 10/2005 | Demarais et al. |
| 2005/0240279 A1 | 10/2005 | Kagan et al. |
| 2005/0247320 A1* | 11/2005 | Stack et al. .................. 128/898 |
| 2005/0250980 A1* | 11/2005 | Swanstrom et al. ............ 600/37 |
| 2005/0251158 A1 | 11/2005 | Sadat et al. |
| 2005/0251159 A1* | 11/2005 | Ewers et al. .................. 606/153 |
| 2005/0251161 A1 | 11/2005 | Saadat et al. |
| 2005/0251162 A1* | 11/2005 | Rothe et al. .................. 606/153 |
| 2005/0251176 A1* | 11/2005 | Swanstrom et al. .......... 606/153 |
| 2005/0251177 A1* | 11/2005 | Saadat et al. ................. 606/153 |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1* | 12/2005 | Stack et al. .................. 606/153 |
| 2005/0267595 A1 | 12/2005 | Chen et al. |
| 2005/0267596 A1 | 12/2005 | Chen et al. |
| 2005/0273060 A1 | 12/2005 | Levy et al. |
| 2005/0283107 A1 | 12/2005 | Kalanovic et al. |
| 2006/0015006 A1 | 1/2006 | Laurence et al. |
| 2006/0020278 A1 | 1/2006 | Burnette et al. |
| 2006/0058829 A1 | 3/2006 | Sampson et al. |
| 2006/0100643 A1 | 5/2006 | Laufer et al. |
| 2006/0129094 A1 | 6/2006 | Shah |
| 2006/0135971 A1* | 6/2006 | Swanstrom et al. .......... 606/153 |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0157067 A1* | 7/2006 | Saadat et al. ................. 128/898 |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0027548 A1 | 2/2007 | Levine et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1* | 8/2007 | Baker et al. .................. 606/153 |
| 2007/0198074 A1 | 8/2007 | Dann et al. |
| 2007/0219571 A1* | 9/2007 | Balbierz et al. ............. 606/153 |
| 2007/0239284 A1 | 10/2007 | Skerven et al. |
| 2007/0260327 A1 | 11/2007 | Case et al. |
| 2007/0276428 A1 | 11/2007 | Haller et al. |
| 2007/0276432 A1 | 11/2007 | Stack et al. |
| 2008/0033574 A1 | 2/2008 | Bessler et al. |
| 2008/0065122 A1* | 3/2008 | Stack et al. .................. 606/151 |
| 2008/0116244 A1 | 5/2008 | Rethy et al. |
| 2008/0190989 A1 | 8/2008 | Crews et al. |
| 2008/0208355 A1 | 8/2008 | Stack et al. |
| 2008/0294179 A1 | 11/2008 | Balbierz et al. |
| 2008/0319471 A1 | 12/2008 | Sosnowski et al. |
| 2009/0024143 A1 | 1/2009 | Crews et al. |
| 2009/0030284 A1 | 1/2009 | Cole et al. |
| 2009/0125040 A1 | 5/2009 | Hambly et al. |
| 2009/0182424 A1 | 7/2009 | Marco et al. |

FOREIGN PATENT DOCUMENTS

| | | |
|---|---|---|
| EP | 0 775 471 | 5/1997 |
| EP | 1 492 478 | 1/2005 |
| EP | 1 602 336 | 12/2005 |
| FR | 2768324 | 3/1999 |
| JP | 09-168597 | 6/1997 |
| WO | WO91/01117 | 2/1991 |
| WO | WO95/25468 | 9/1995 |
| WO | WO97/47231 | 12/1997 |
| WO | WO00/12027 | 3/2000 |
| WO | WO00/32137 | 6/2000 |
| WO | WO00/78227 | 12/2000 |
| WO | WO01/45485 | 6/2001 |
| WO | WO01/49359 | 7/2001 |
| WO | WO01/66018 | 9/2001 |
| WO | WO01/85034 | 11/2001 |
| WO | WO01/89393 | 11/2001 |
| WO | WO02/060328 | 8/2002 |
| WO | WO03/017882 | 3/2003 |
| WO | 03/086246 | 10/2003 |
| WO | WO03/086246 | 10/2003 |
| WO | WO03/086247 | 10/2003 |
| WO | WO03/090633 | 11/2003 |
| WO | WO03/094784 | 11/2003 |
| WO | WO03/094785 | 11/2003 |
| WO | WO03/099137 | 12/2003 |
| WO | WO2004/019765 | 3/2004 |
| WO | WO2004/019787 | 3/2004 |
| WO | WO2004/032760 | 4/2004 |
| WO | WO2004/037064 | 5/2004 |
| WO | WO2004/041133 | 5/2004 |
| WO | WO2004/064680 | 8/2004 |
| WO | WO2004/064685 | 8/2004 |
| WO | WO2004/080336 | 9/2004 |
| WO | WO2004/110285 | 12/2004 |
| WO | WO2005/037152 | 4/2005 |
| WO | WO2005/074894 | 8/2005 |
| WO | WO2005/079673 | 9/2005 |
| WO | WO2005/096991 | 10/2005 |
| WO | WO2005/105003 | 11/2005 |
| WO | WO2006/016894 | 2/2006 |
| WO | 2006/055365 | 5/2006 |
| WO | WO2006/055365 | 5/2006 |
| WO | WO2006/127593 | 11/2006 |
| WO | WO2007/041598 | 4/2007 |
| WO | WO2008/030403 | 3/2008 |
| WO | WO2008/033409 | 3/2008 |
| WO | WO2008/033474 | 3/2008 |
| WO | WO2008/141288 | 11/2008 |
| WO | WO2009/011881 | 1/2009 |
| WO | WO2009/011882 | 1/2009 |

OTHER PUBLICATIONS

International Search Report from PCT Patent Application No. PCT US/2003/004378 mailed Aug. 13, 2003.
International Search Report from PCT Patent Application No. PCT/US2003/0033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US20004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
International Search Report from PCT Patent Application No. PCT/US2007/019833 mailed Feb. 20, 2008.
International Search Report from PCT Patent Application No. PCT/US2007/019940 mailed Mar. 14, 2008.
International Search Report and Written Opinion for PCT application PCT/US2008/008726, Oct. 16, 2008.
International Search Report of PCT Patent Application No. PCT/US2008/063440 mailed Aug. 1, 2008.

(56) References Cited

OTHER PUBLICATIONS

International Search Report for PCT application PCT/US2008/008729, Jul. 17, 2008.
Felsher, et al., "Mucosal Apposition in Endoscopic Suturing", Gastrointestinal Endoscopy, vol. 58, No. 6, pp. 867-870, (2003).
Stecco, K. et al., "Trans-Oral Plication Formation and Gastric Implant Placement in a Canine Model", Stecco Group, San Jose and Barosense, Inc., Redwood City, California (2004).
Stecco, K. et al., "Safety of a Gastric Restrictive Implany in a Canine Model", Stecco Group, San Jose and Barosense, Inc., Redwood City, California (2004).

* cited by examiner

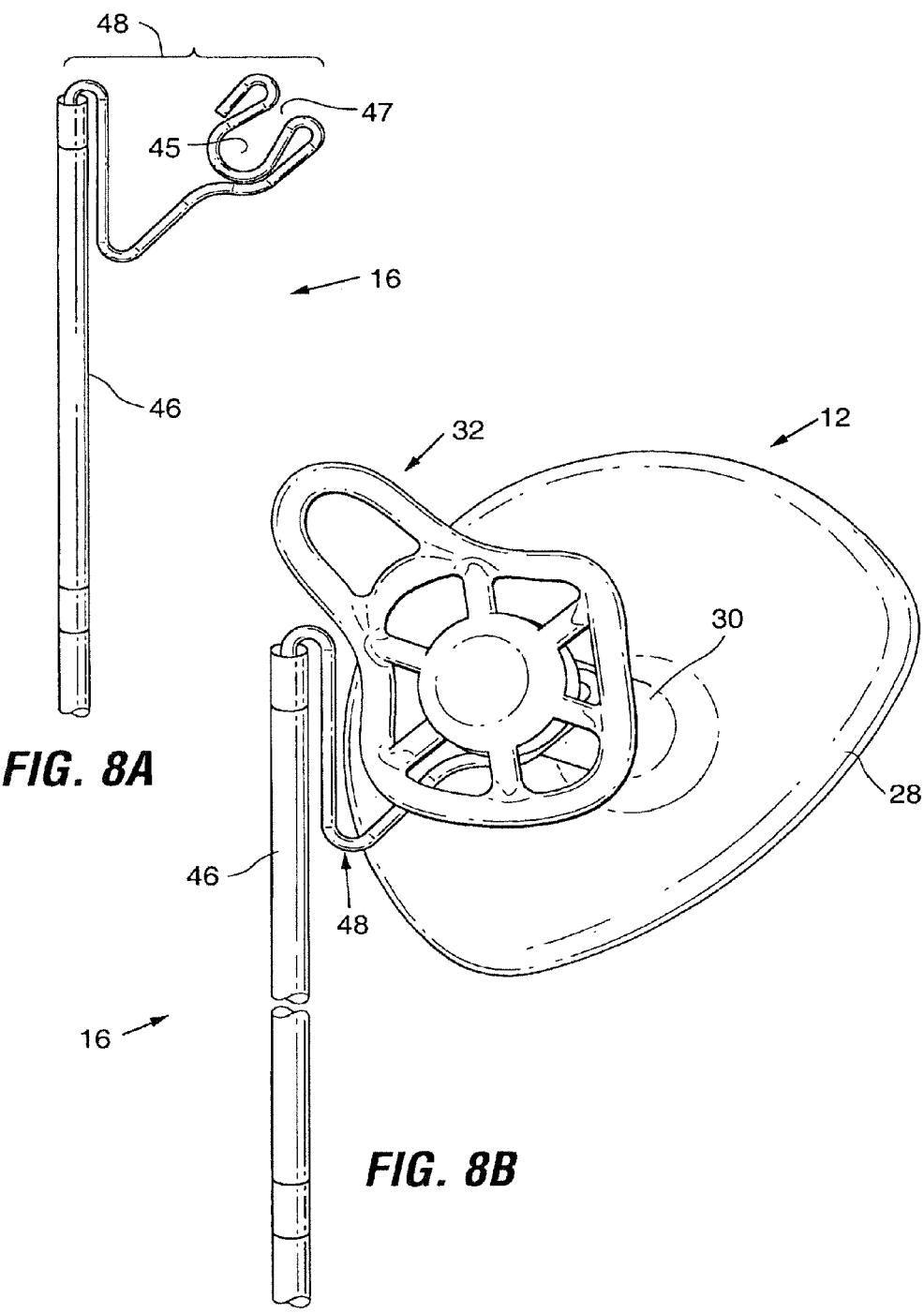

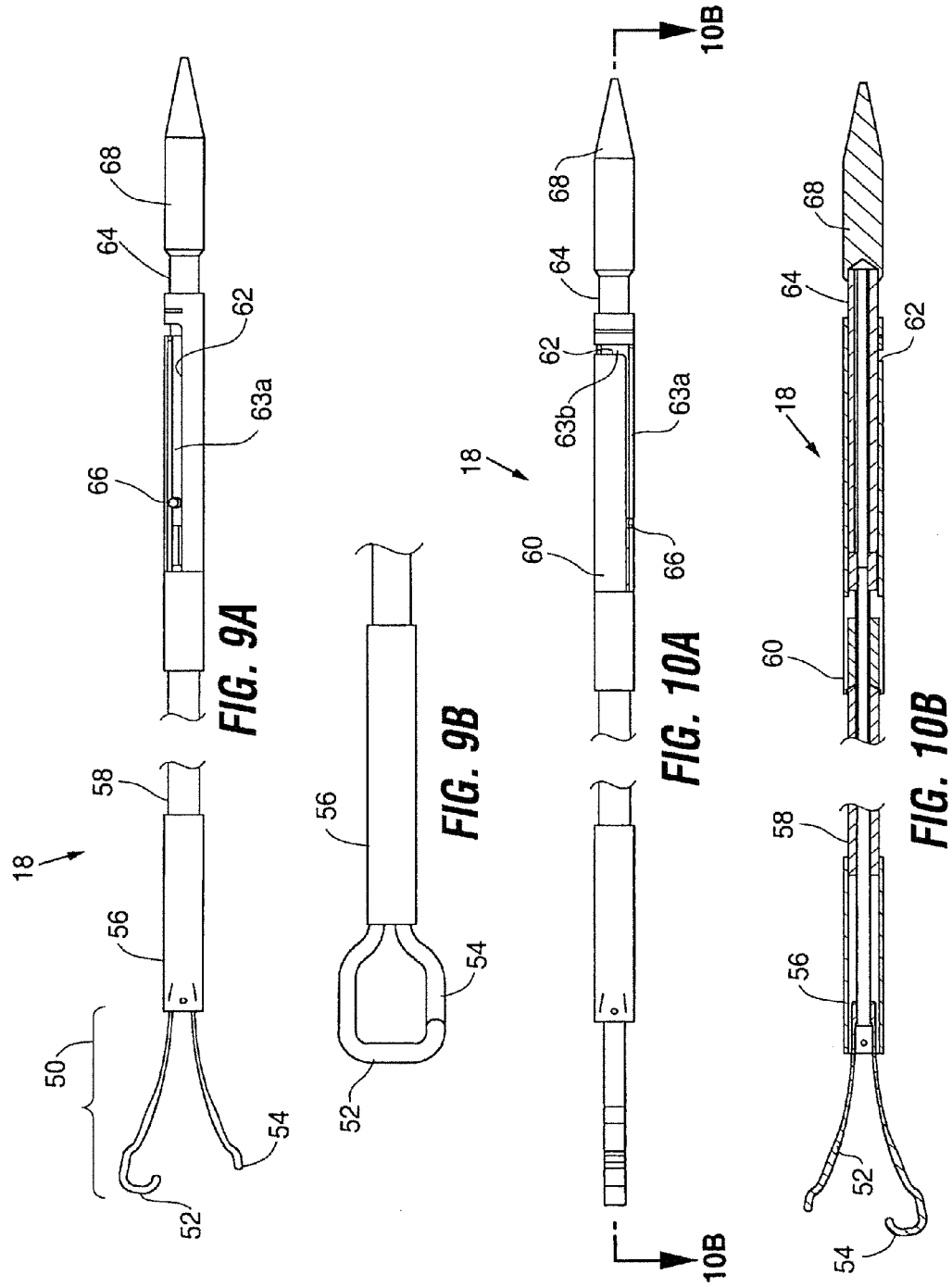

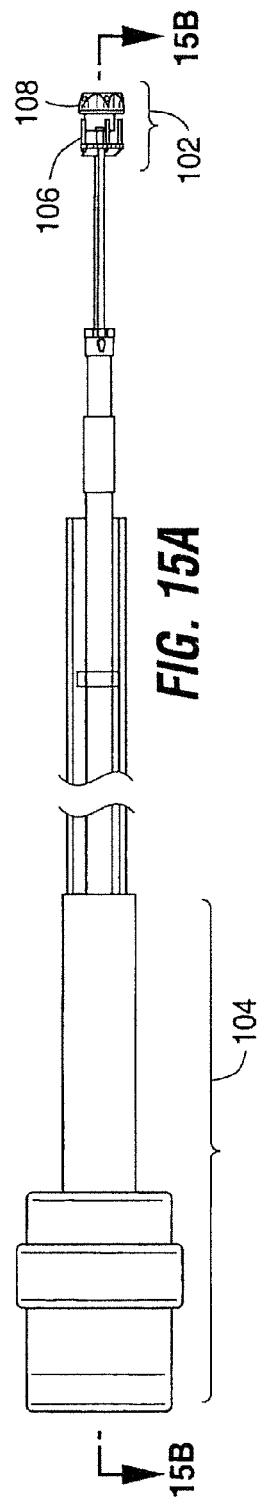
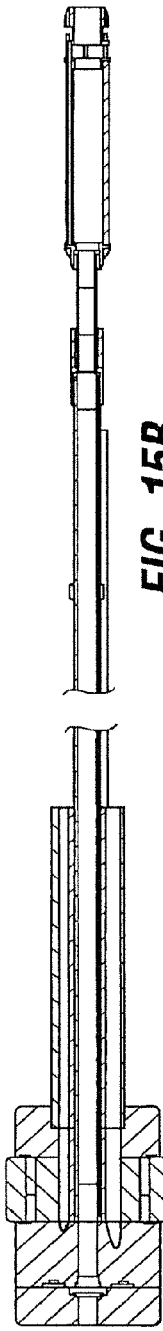
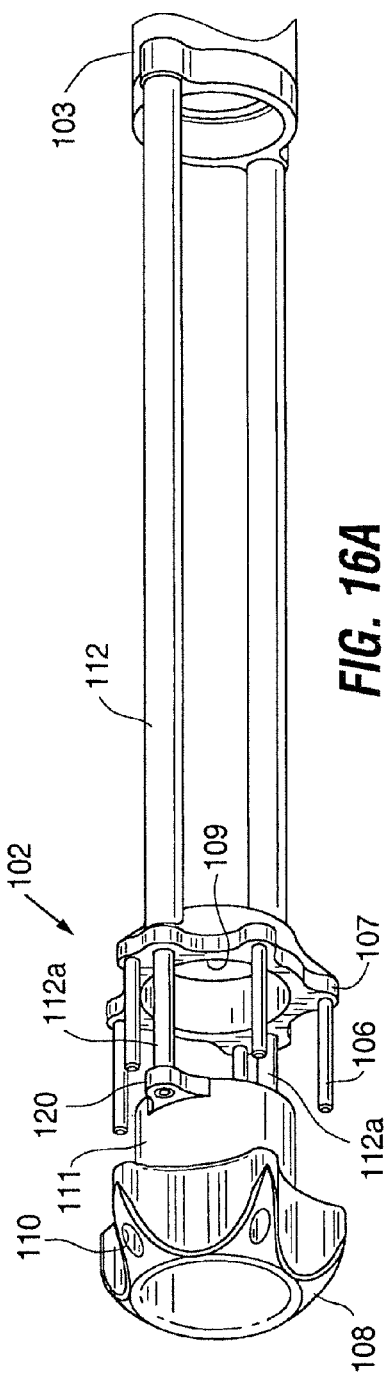

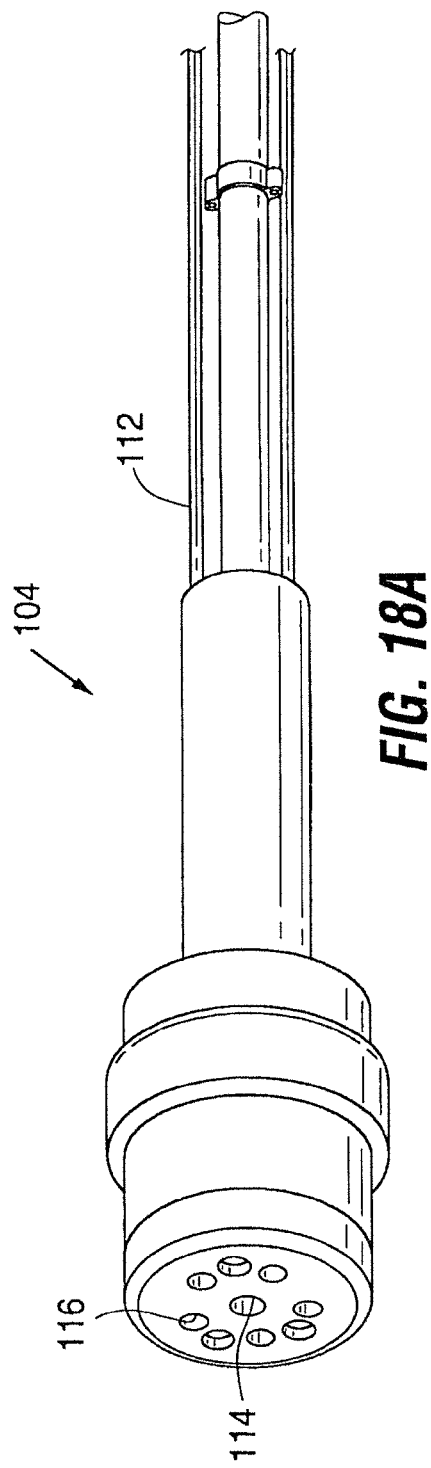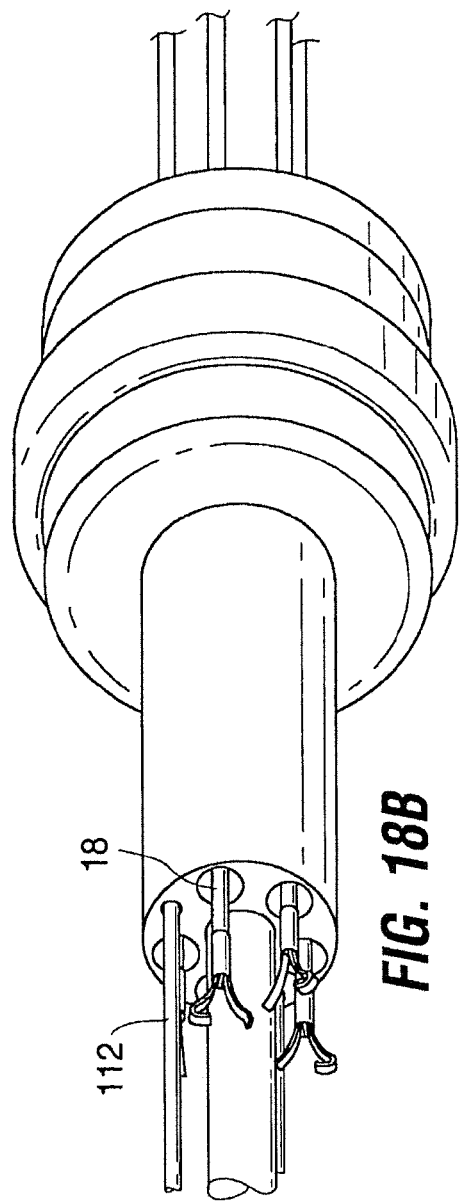
FIG. 18A
FIG. 18B

ENDOSCOPIC IMPLANT SYSTEM AND METHOD

PRIORITY

This is application is a divisional of U.S. Ser. No. 12/175,242 filed Jul. 17, 2008, which claims priority to U.S. Provisional Application No. 60/950,584, filed Jul. 18, 2007, and U.S. Provisional Application No. 61/042,862, filed Apr. 7, 2008.

TECHNICAL FIELD OF THE INVENTION

The present invention relates to the field of systems for use in endoscopically implanting devices within the gastro-intestinal system.

BACKGROUND

An anatomical view of a human stomach S and associated features is shown in FIG. 1. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Several prior applications, including U.S. Publication No. U.S. 2007/0276432 having a priority date of Oct. 8, 2004 and U.S. Publication No. U.S. 2008/0065122, filed May 23, 2006 describe methods according to which medical implants are coupled to tissue structures, such as plications or folds, formed within the stomach. Examples of methods and devices for forming such tissue structures are described in U.S. Publication No. U.S. 2007/0219571 (entitled ENDOSCOPIC PLICATION DEVICES AND METHOD), filed Oct. 3, 2006, U.S. application Ser. No. 11/900,757 (entitled ENDOSCOPIC PLICATION DEVICE AND METHOD), filed Sep. 13, 2007, and U.S. application Ser. No. 12/050,169 (entitled ENDOSCOPIC STAPLING DEVICES AND METHODS), filed Mar. 18, 2008. Each of the referenced publications and applications is incorporated herein by reference.

As disclosed in these prior applications, more robust and long lasting coupling between the implant and the surrounding stomach wall tissue is achieved when the plications/folds are formed by retaining regions of serosal tissue (i.e., the tissue on the exterior surface of the stomach) in contact with one another. Over time, adhesions form between the opposed serosal layers. These adhesions help to create strong bonds that can facilitate retention of the plication/fold over extended durations, despite the forces imparted on them by stomach movement and implanted devices Several of the disclosed methods for forming tissue plications include a step in which a hole or cut is formed in the plication, using the plication device or other devices. An example of this type of plication is shown in FIG. 2A. This application discloses a system for attaching a medical implant to cutouts of this type, or to other types of openings in the plications (e.g., cuts, slits, perforations, tissue tunnels, etc.).

BRIEF DESCRIPTION OF THE DRAWINGS

FIG. 8A is a perspective view of an anchor hand-off tool.

FIGS. 8B, 8C, and 8D are perspective views showing the anchor coupled to the anchor hand-off tool.

FIG. 9A is a side elevation view of an anchor grasper in the open position.

FIG. 9B shows the distal end of the anchor grasper of FIG. 9A in the closed position.

FIG. 10A is a top plan view of the anchor grasper of FIG. 9A.

FIG. 10B is a cross-section view taken along the plane designated 10B-10B in FIG. 10A.

FIG. 15A is a side elevation view of a restrictor guide.

FIG. 15B is a cross-section view of the restrictor guide taken along the plane designated 15B-15B in FIG. 15A.

FIG. 16A is a perspective view of the distal portion of the restrictor guide, showing the mount in the open configuration.

FIG. 18A is a perspective view showing the proximal end of the restrictor guide.

FIG. 18B is a perspective view showing the distal portion of the multi-lumen portion of the restrictor guide.

DETAILED DESCRIPTION

Figure 1:
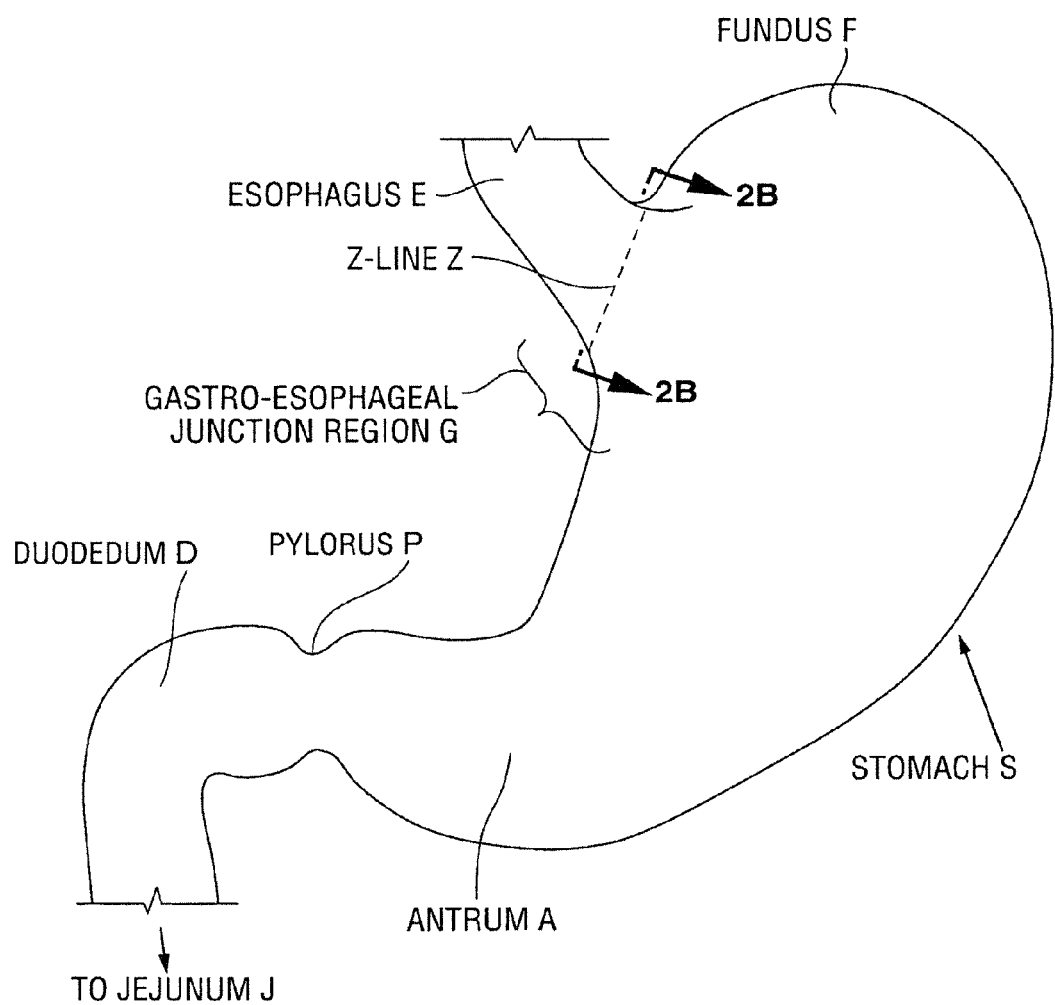
FIG. 1 is a schematic illustration of a human stomach and a portion of the small intestine.
Figure 2A:
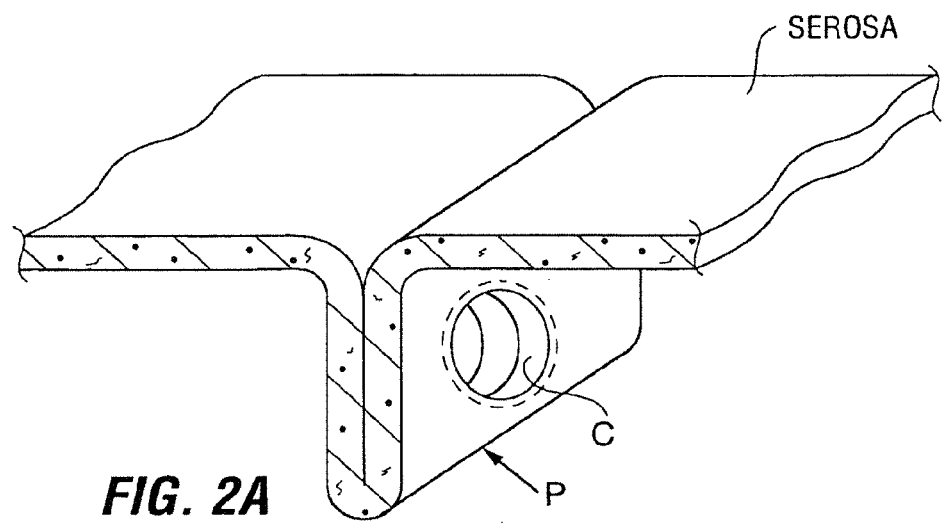
FIG. 2A is a partial section of a stomach wall showing a stomach wall plication having an opening formed in it.
Figure 2B:
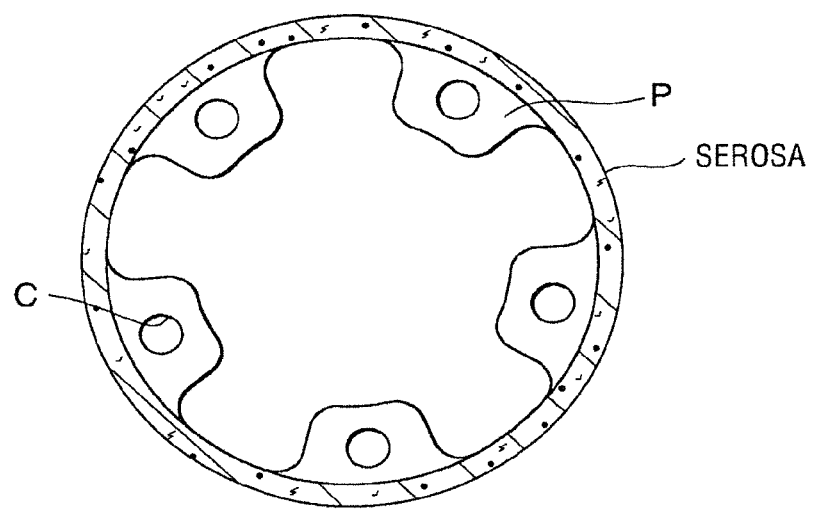
FIG. 2B is a cross-section view taken along the plane designated 2B-2B in FIG. 1, and illustrating five plications formed in a gastro-esophageal junction region of the stomach.

FIG. 2B is a schematic cross-section view of the stomach, looking distally into the stomach interior. In this view, five tissue plications P having openings such as cutouts C are shown to have been formed in the stomach wall tissue. This view would seem to illustrate clear access via the esophagus to the plications and cutouts using endoscopic instruments. However, the natural undulations and folds of the actual stomach tissue, and the constant movement of the stomach, limit the visibility of the cutouts and even the plications themselves, rendering it difficult to endoscopically access the cutouts in an actual human subject. The disclosed system facilitates access to the cutouts, and provides for an efficient method for coupling an implant to the cutouts.

Figure 3:
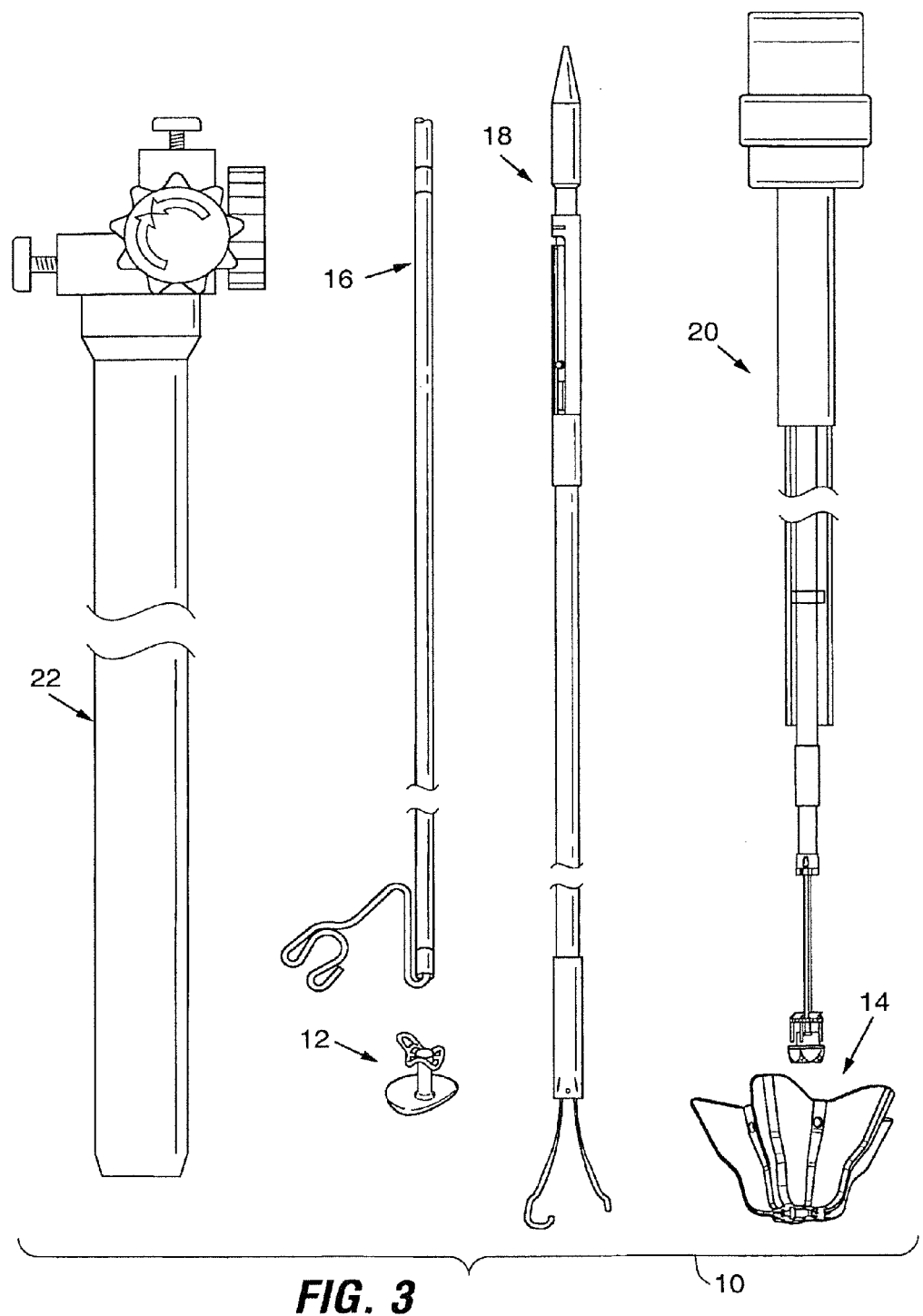
FIG. 3 shows an endoscopic implant system.

FIG. 3 illustrates an embodiment of an endoscopic implant system 10 that may be used for this purpose. In general, system 10 includes multiple anchors 12 (one shown) that are implanted in the cutouts and an implant 14 to be coupled to the anchors 12. The implant can be any type of implant to be anchored within the stomach. In the disclosed embodiment, the implant is a restrictor 14 designed to slow the rate at which food can enter the stomach from the esophagus.

An anchor hand-off 16 delivers the anchors into the stomach, and anchor graspers 18 (one shown) are used to position the anchors within the tissue openings and also to guide the restrictor 14 to the implanted anchors. A restrictor guide 20 is provided for advancing the restrictor into position in the stomach. An endogastric overtube 22 is provided for establishing a working channel between the mouth and the stomach. Other tools shown elsewhere in the drawings, such as a multi-lumen guide 24 (FIG. 19A), articulated guides 25 (FIG. 19A), and one or more endoscopes 26 (FIG. 19A) are additionally provided.

Anchor

Figure 4A:
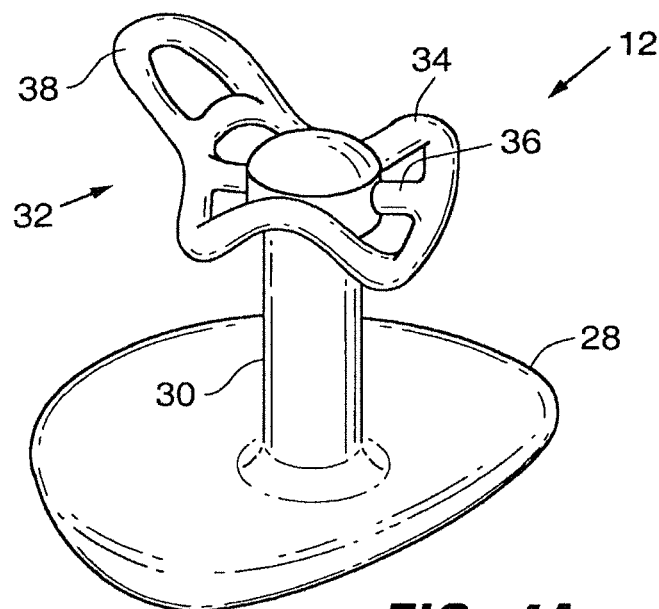
FIG. 4A is a perspective view of the anchor of the implant system of FIG. 3.
Figure 4B:
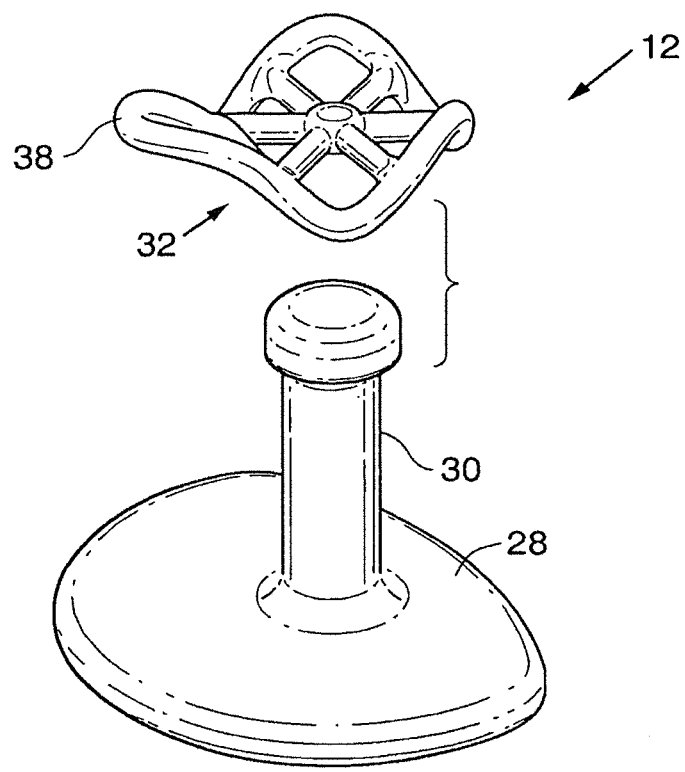
FIG. 4B is a perspective view of the anchor of FIG. 4A, showing the head separated from the stem.

One embodiment of an anchor 12 is shown in FIG. 4. A preferred anchor will pass though the opening C in the plication cutout with relative ease and minimal tissue trauma, but will resist pulling out of the opening in the cutout when subjected to the stresses imparted to it by the restrictor. Moreover, a preferred anchor will minimize the stress and strain on the stomach wall and distribute a given stress as evenly as possible so as to prevent the stomach's natural defense from engaging in an attempt to eliminate the anchors and restrictor.

Referring to FIG. 4A, the general features of the anchor 12 include a base 28, a stem 30, and a head 32. The anchor is formed using materials that are durable within the stomach environment. In one embodiment, the head 32 is molded out of a higher durometer compliant material (such as 50 shore A durometer Silicone) while the stem 30 and base 28 are molded out of a softer compliant material (such as 5 shore A durometer Silicone). Since the loading on the anchor from the restrictor implant can be seen as shear against the edges of the opening in the plication, the stern 30 is formed to have a relatively large diameter (2 mm-8 mm) to minimize stress and abrasion on the stomach wall tissue inside the opening. The edges of the anchor are molded with generous fillet radii to minimize abrasion of stomach wall tissue.

Figure 20A:
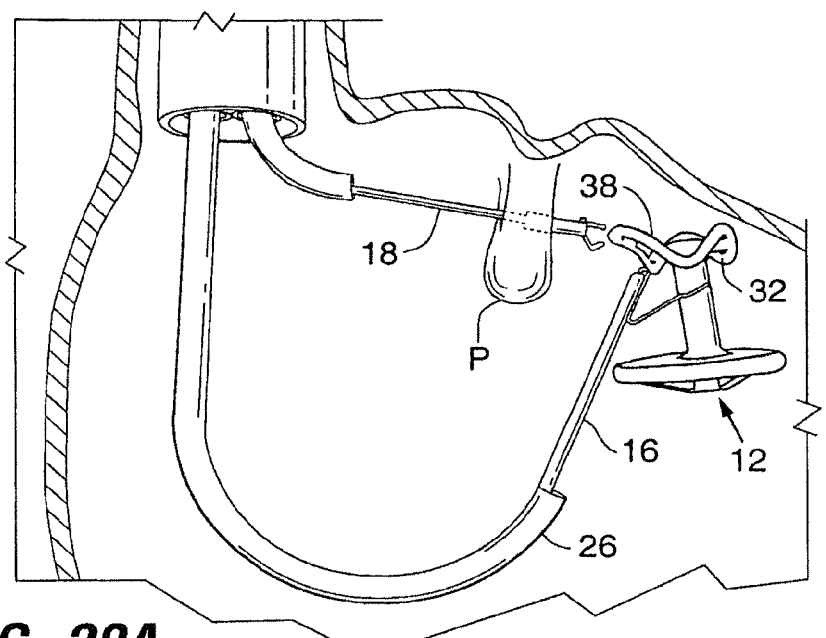
FIGS. 20A, 20B, 20C, 20D, 20E, and 20F schematically illustrate transfer of the anchor from the anchor hand-off to the anchor grasper within the stomach.
Figure 20B:
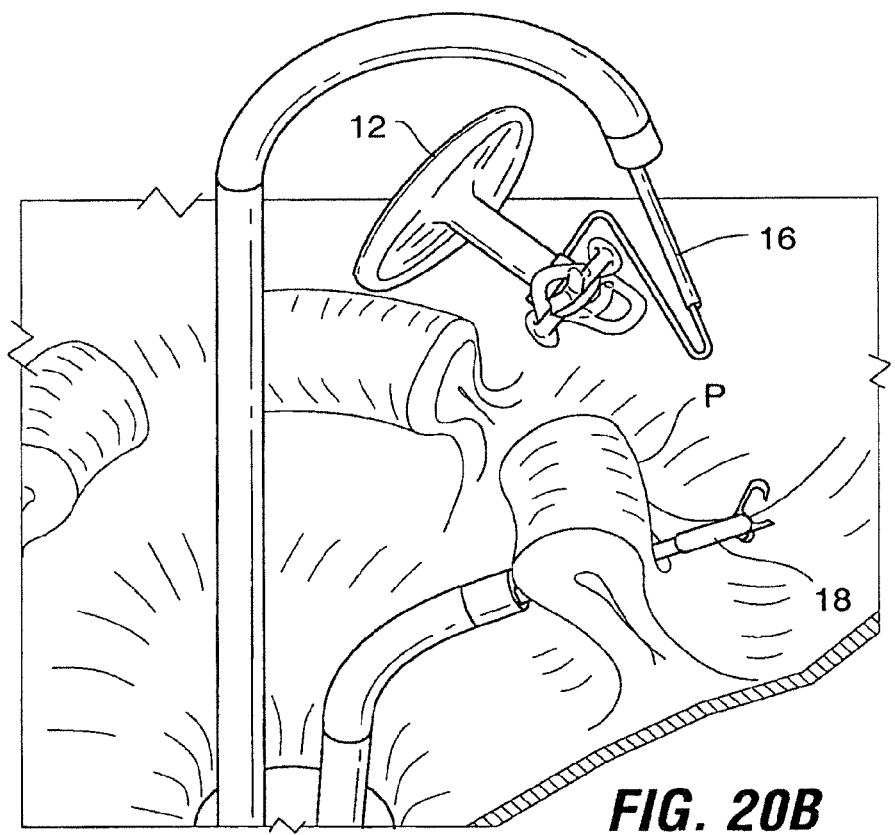
Figure 20C:
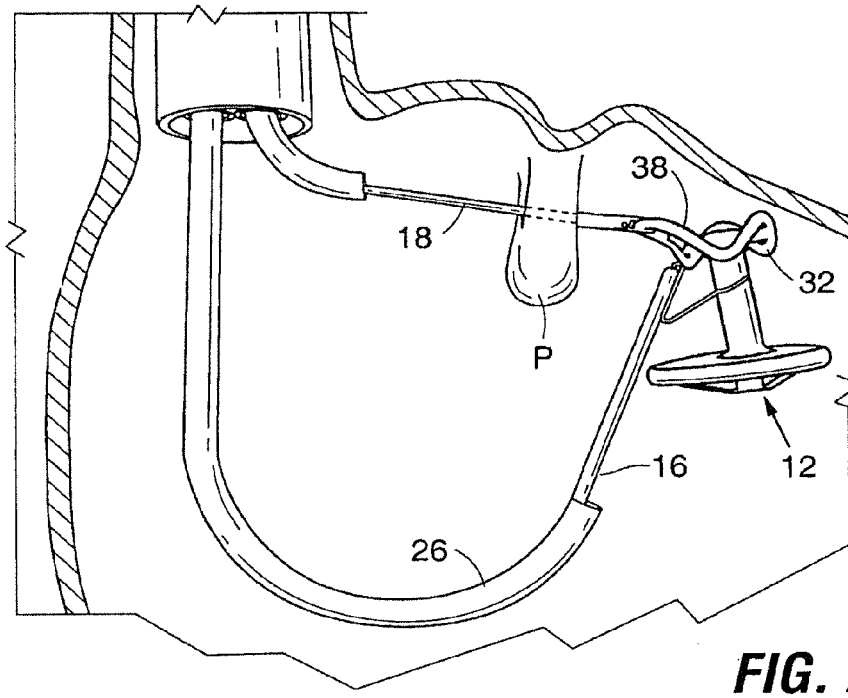
Figure 20D:
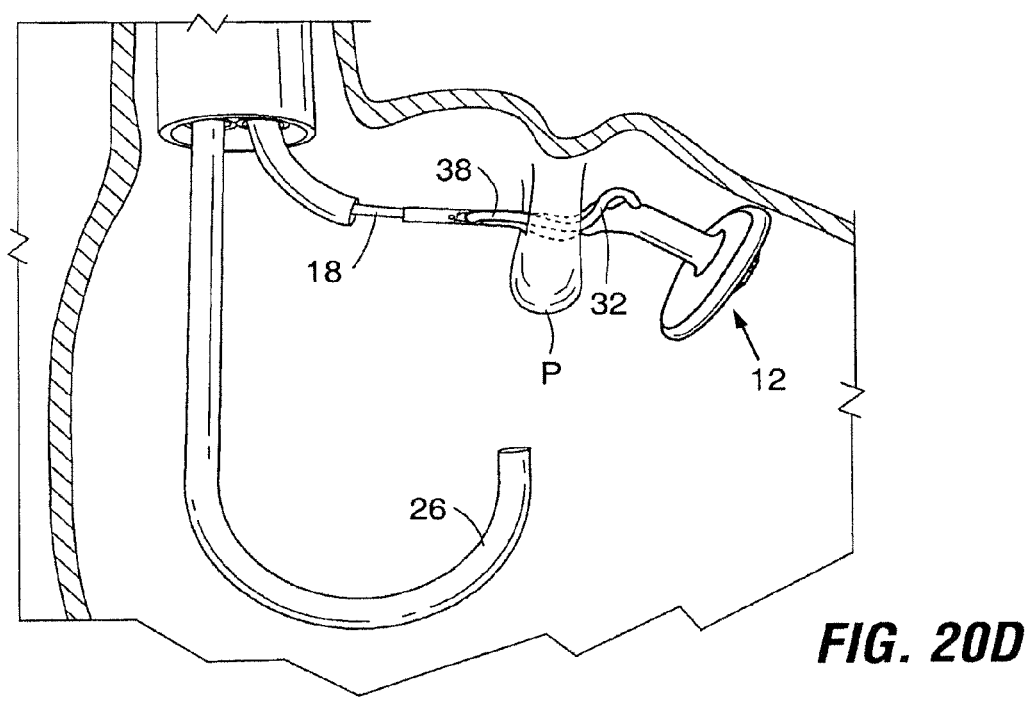
Figure 20E:
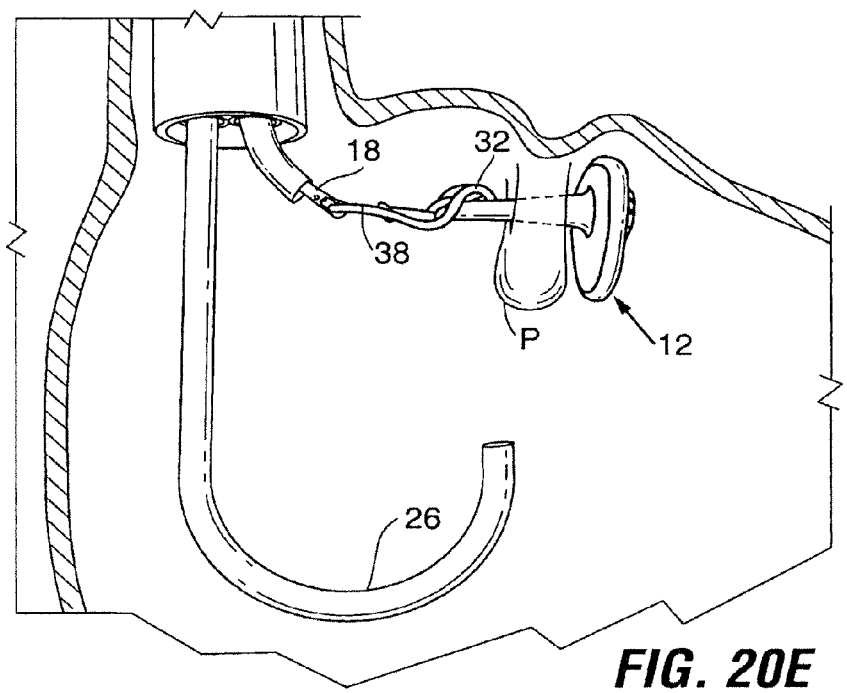

Head 32 includes a ring 34 and a plurality of struts 36 coupling the ring 34 to the stem 30, and an elongate loop 38 extending from the ring 34. The anchor is elastically deformable to an elongated shape (see FIGS. 20D and 20E) in response to application of tension to the ring 34 or loop 38 (collectively referred to as the "rim"). This allows the anchor to be drawn into a streamlined shape so that it can be drawn through the opening in the plication and also through an opening in the restrictor. When the anchor is pulled from the rim, its shape lengthens and slims down to fit through a much smaller hole. For example in one embodiment, in its natural state the anchor has an outer head diameter of approximately 0.600 inch (15 mm), but in its streamlined orientation it can fit through a plication opening of 0.200 inch (5 mm). However, once implanted, the anchor's shape resists pull-out force to a higher degree since the rim is not being pulled and lengthened directly. Also in this embodiment, the base is designed so it will not pull through the hole and may have an outer diameter of approximately 1 inch (25.4 mm)

Figure 5:
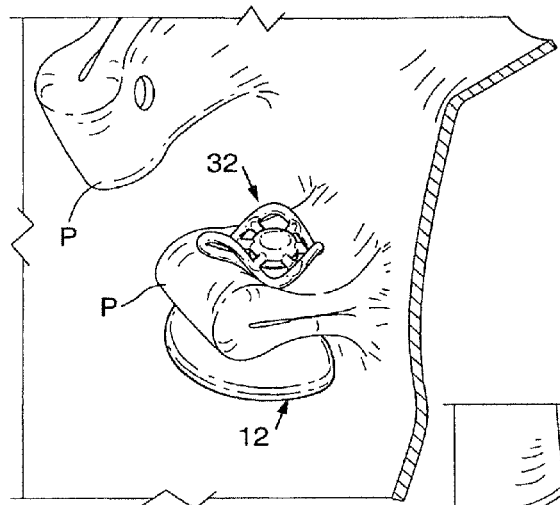
FIGS. 5, 6, and 7 are partial section views of a human stomach schematically illustrating the anchor of FIG. 4A positioned in an opening in a stomach wall plication.

Referring to the top view of the anchor 12 shown in FIG. 5, when an anchor is implanted in a plication opening, the anchor's proximity to the wall of the stomach with its enveloping rugae can make it difficult to find and grab onto the anchor when it is time to couple the restrictor implant to the anchors. The head 32 is shaped to have an undulating profile to enhance its visibility and accessibility when the anchor is positioned in a plication opening. The undulation of the head forces several of the elements of the head away from the wall to make them more visible and also to allow a grasping tool to latch onto one of those elements without also grabbing adjacent tissue.

Figure 6:
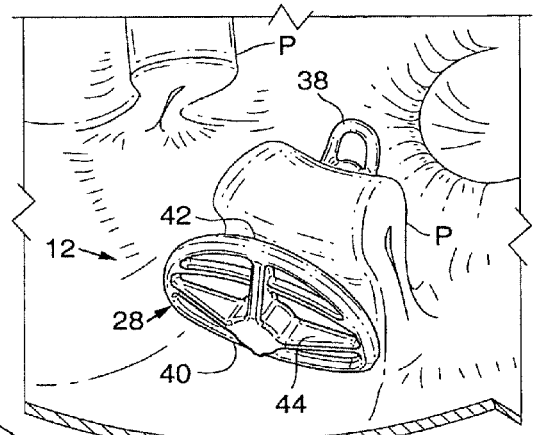
Figure 7:
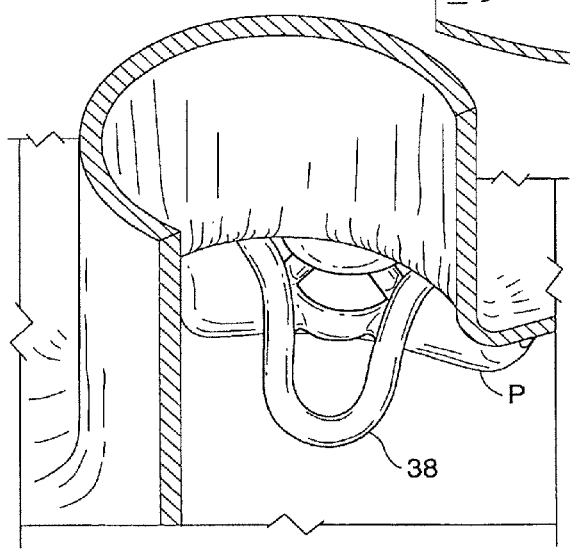

Referring to FIG. 6, the base 28 is preferably formed to have an asymmetrical shape. In the illustrated example, one edge 40 of the base is formed to have a flatter curvature than that of the other edge 42 of the base. When implanted, the anchor self-orients to position the flatter edge 40 against the adjacent stomach wall as shown. Since the loop 38 of the head extends in a direction opposite to the side of the anchor on which the flatter edge 40 is position, this self-alignment causes the loop 38 to extend towards the center of the stomach as shown in FIG. 7. This makes it easier to find segments of the anchor head amongst the folds of the stomach which can envelope other segments.

Referring again to FIG. 6, the base 28 preferably includes a relatively large surface area (e.g., approximately 1 square inch) so as to distribute the stress of holding the restrictive implant in place over a large percentage of the surface area of the tissue plication. Reinforcing ribs 44 may be positioned on the underside of the base, radiating from the stem to the edges of the base, to facilitate distribution of stress while minimizing the overall weight of the base.

Anchor Hand-Off Tool

Anchor hand-off 16 is an instrument used to deliver individual anchors to the implantation site, and to hand-off each anchor to an anchor grasper which pulls the anchor through an opening in a plication.

Referring to FIG. 8A, one embodiment of an anchor hand-off 18 includes a torqueable elongate shaft 46 having a wire element 48 extending from its distal end and attachable to an anchor.

In one embodiment, the anchor hand-off 16 has a horseshoe shaped form with an opening 45 that narrows to form a constriction 47. The stretchable nature of the anchor stem 30 allows it to be squeezed through the constriction 47 and thus held in place by friction. See FIGS. 8B-8D. Upon pulling on the head portion 32 by the anchor grasper, 18, the stem 30 elongates and passes out of the horseshoe shaped constriction.

Shaft 46 is slidably disposed in an articulating guide 49 that will articulate in response to actuation using pull wires or other means known to those skilled in the art. The articulating guide 26 may be one with video capability, for example it might be an articulating endoscope. In one embodiment, wire element 48 is detachable from the shaft 46 of the anchor hand-off 16 to allow shaft 48 to pass through a small diameter tool channel in the articulating guide 26. Once the distal end of the shaft 46 reaches the distal end of the guide 26, the wire element 48 is coupled to the shaft 46.

Figure 8C:
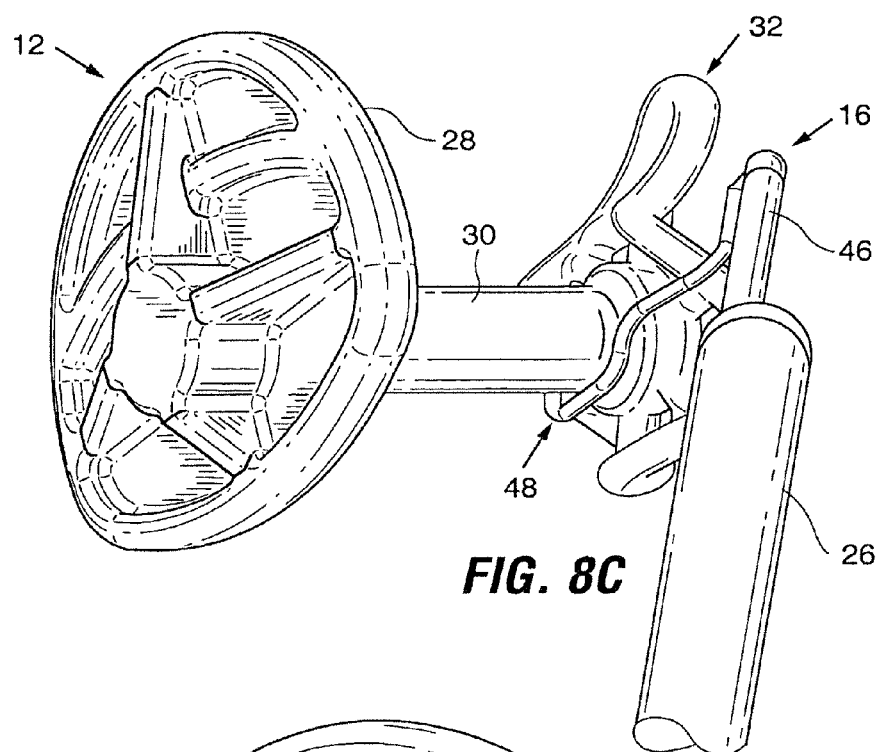
Figure 8D:
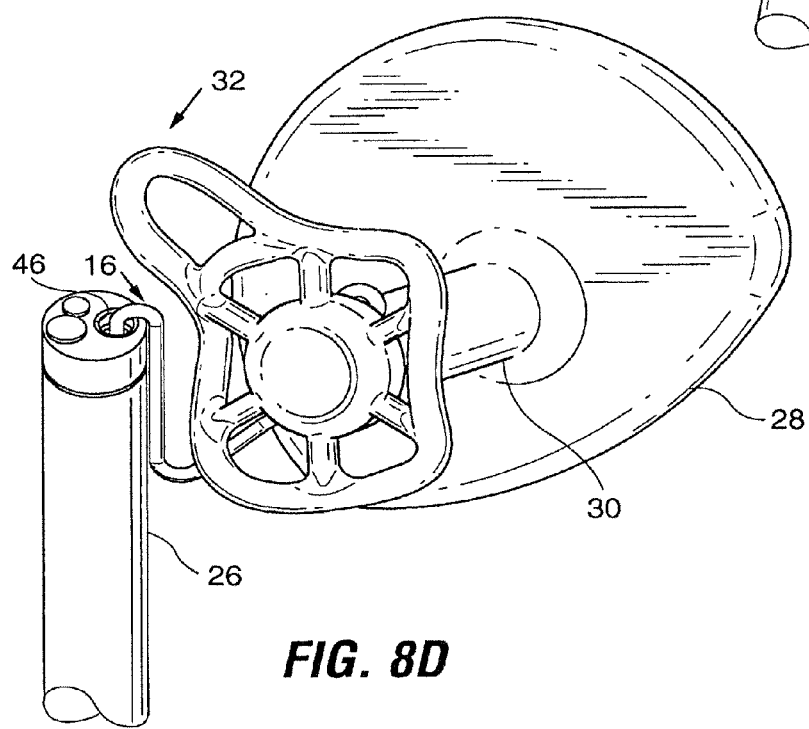

Furthermore, the anchor hand-off tool 16 may be designed to hold the anchor behind (or axially off-set from) the distal tip of the articulating guide 26 with video capability. This facilitates greater visibility at the target site/plication by positioning the held anchor out of the endoscope's field of view as shown in FIGS. 8C and 8D. To perform the actual hand-off of the anchor 12, the user can extend and torque the hand-off tool 16 to position at least a portion of the anchor head 32 within the field of view.

Anchor Grasper Tool

Anchor grasper 18 is designed to couple to or engage a portion of the head 32 of an anchor 12. It is used to pull the anchor 12 through an opening in a plication, and to pull the anchor through a corresponding opening in a restrictor that is to be implanted. The anchor grasper 18 may have a variety of designs that allow these functions to be carried out. One such design is shown in FIGS. 9A and 9B an employs a coupling/grasping element 50 that takes the form of a hook 52 having a gate 54 that closes against the opening in the hook 52. The hook and gate are naturally biased in the open position shown in FIG. 9A.

A closure tube 56 is longitudinally slidable over the hook and gate to lock them in the closed position, thus preventing them from separating. The collar and associated features are proportioned to ensure that when the grasping element 50 is to be locked, bending of the shaft of the anchor grasper 18 does not cause the closure tube 56 to slide into a position that will release the grasping element 50 from the locked position.

Referring to FIG. 10B, the closure tube 56 is mounted to a torqueable element 58 (preferably a coil), which in turn is coupled to outer tubing 60. An L-shaped slot 62 is formed in the outer tubing 60. As best shown in FIG. 10A, slot 62 includes a longitudinal segment 63a and a partially circumferential segment 63b.

Hypotube 64 is slidably and rotatably disposed within outer tubing 60, and includes a pin 66 disposed within the slot 62. Hypotube 64 is mounted to a tapered handle 68. A cable 70 has a distal end coupled to the grasping element 50 and a proximal end mounted to the handle 68.

To close and lock the grasping element, the outer tube 60 is advanced distally relative to the handle 68. Advancement of the outer tube 60 pushes the coil 58 and thus the closure tube 56 in a distal position until the closure tube 56 moves the grasping element 50 to the closed position shown in FIG. 9B. As the outer tube 60 moves distally, longitudinal segment 63a of the slot 62 slides over pin 66. The outer tube 60 is then rotated to cause positioning of pin 66 within the circumferential segment 63b of the slot 62, and to thereby lock the outer tube 60 in the distal position. To unlock the grasper element 50, the outer tube 60 is rotated in the opposite direction to release the pin 66 from the circumferential segment 63b. Since the closure tube is no longer locked in the distal position, the grasping element 50 moves to the open position due to its natural bias, thereby pushing the outer tube 60 in a proximal direction.

Figure 11A:
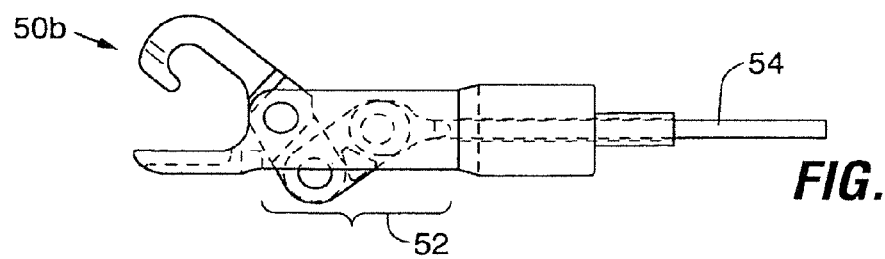
FIGS. 11A and 11B are side elevation views of the distal end of an alternative anchor grasper.
Figure 11B:
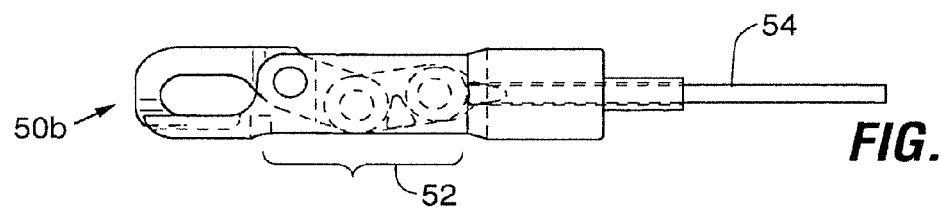

FIGS. 11A and 11B show an alternative grasper element 50a which is moved between open and closed positions using a system 72 of linkages pivoted using a longitudinally slidable push rod 74.

Restrictor

The restrictor is an implant designed to slow the passage of food from the esophagus into the stomach. The illustrated embodiments, the restrictor is positioned in the stomach such that food enters the restrictor through a proximal opening and exits the restrictor through a distal opening. The restrictor and/or openings are proportioned to slow the rate at which food can move into or through the restrictor, and/or from the restrictor into the rest of the stomach.

A preferred restrictor is proportioned to be coupled to anchors that have been coupled to plications in the gastroesophageal junction region of the proximal stomach. In a preferred design, the restrictor 14 includes features that minimize pulling against the anchors when the restrictor encounters stress as a result of food moving through the restrictor and/or movement of the stomach. Minimizing pulling at the anchors is beneficial for minimizing stress on the stomach wall tissue coupled to the anchors. In general, the restrictor 14 is designed to have compliance between the anchor points (i.e., the points at which the implant is coupled to the tissue directly or using the anchors). This compliance may be achieved using the geometry of the restrictor 14 and/or using restrictor materials selected to give compliance between anchor points.

Figure 12A:
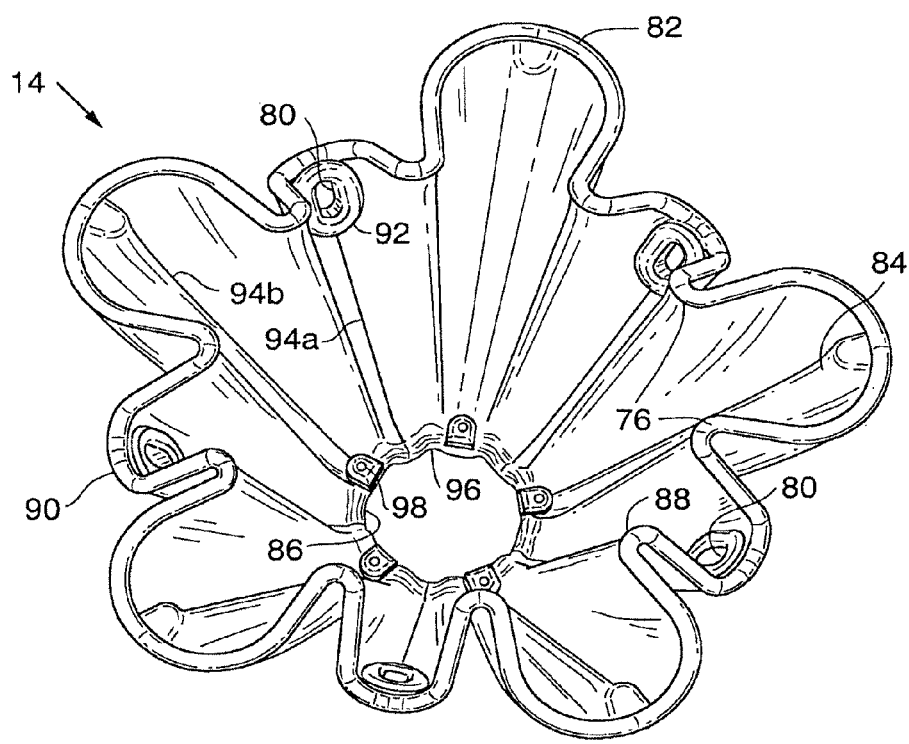
FIG. 12A shows a top perspective view of a first embodiment of a restrictor.
Figure 12B:
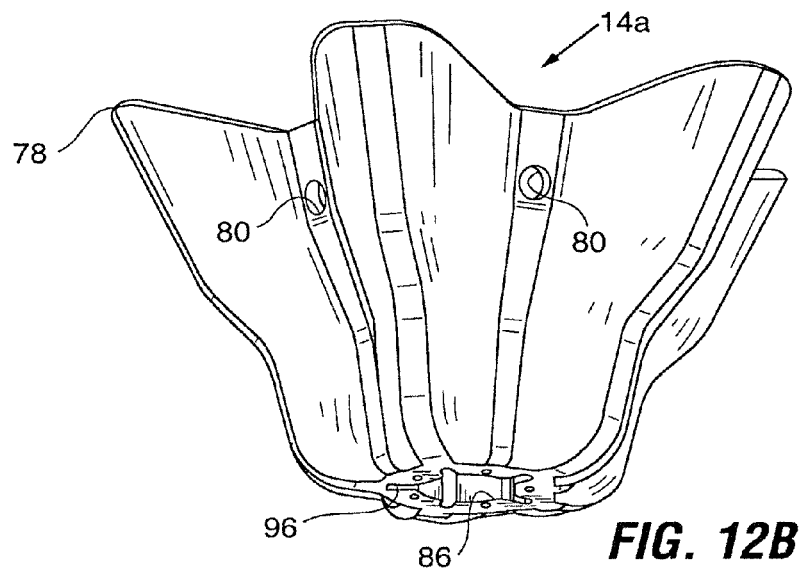
FIG. 12B shows a side perspective view of a second embodiment of a restrictor.

In a first embodiment shown in FIG. 12A, the restrictor 14 is a sleeve having a wall and a plurality of anchor openings 80 formed in the wall. The restrictor wall is an undulating wall defining multiple folds 76 that give it compliance even when molded from a relatively more stiff material (such as 30 shore A silicone). When viewed from the side (see the second embodiment 14a in FIG. 12B), it can be seen that the proximal edge of the restrictor 14 undulates to define peaks 78 in the profile of the proximal edge. When viewed from the top (FIG. 12A), it can be seen that the circumferential profile of the restrictor also includes peaks 82 extending radially outwardly. These peaks 82 define chutes 84 extending from the proximal peaks 78 towards a distal orifice 86. When the restrictor is implanted, the chutes 84 help to channel ingested material towards the distal orifice 86.

Anchor openings 80 are positioned between the radial peaks 82. These openings may be positioned in the portion of the wall that is at the most radially inward position as on the restrictor 14a of FIG. 12B, or the undulations in the wall may be such that the openings 80 are in a section of wall that is positioned between some inwardly extending folds 88 as in FIG. 12A (or that, in other words, forms smaller radial peaks 90 than the radial peaks 82).

Openings 80 may be surrounded by reinforced sections 92 formed using thicker regions of silicone, or a stronger material embedded in or attached to the silicone. Additional reinforcements such as ribs 94a, 94b may extend from the openings 80 towards the orifice 86 and/or from the proximal peaks 78 towards the orifice 86 and may be formed using similar techniques.

The edge of the wall defining the orifice 86 preferably includes folds or undulations 96, allowing the orifice to be compliant as well. In addition, small holes 98 are arranged around the orifice to allow the restrictor 14 to be coupled to the restrictor guide used to deliver the restrictor into the stomach.

Figure 12C:
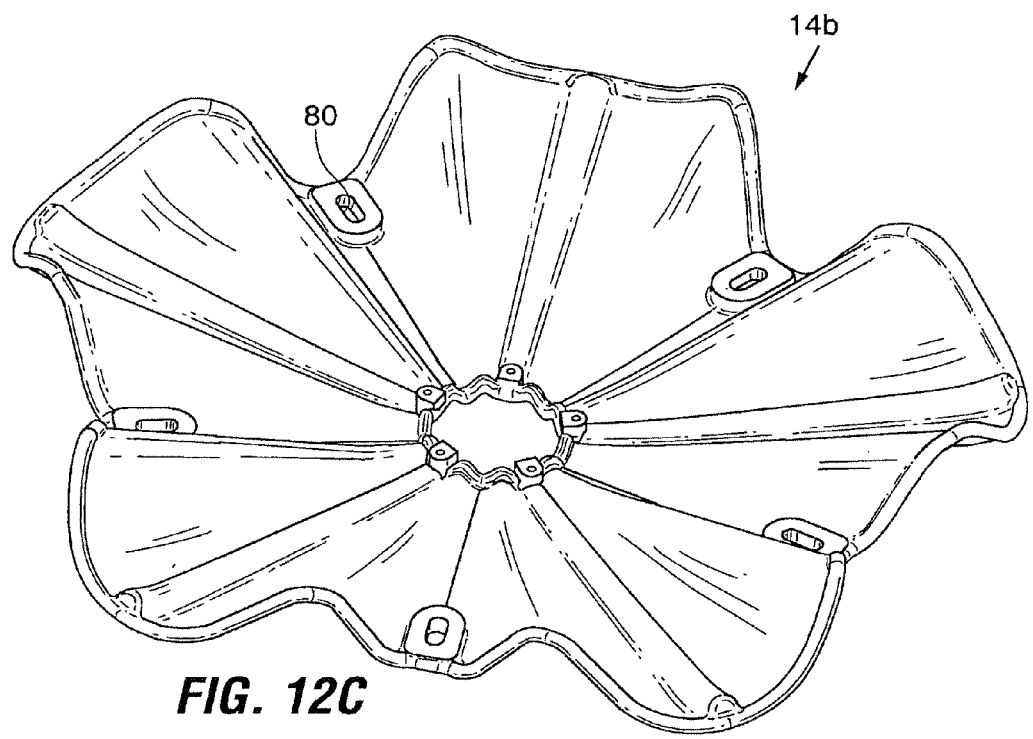
FIG. 12C shows a top perspective view of a third embodiment of a restrictor.

An alternative restrictor 14b shown in FIG. 12C is similar to the restrictor of FIG. 12A, but is molded to be flat for ease of manufacturing, but assumes its undulating configuration at the folds when coupled to anchors at anchor openings 80.

Figure 13:
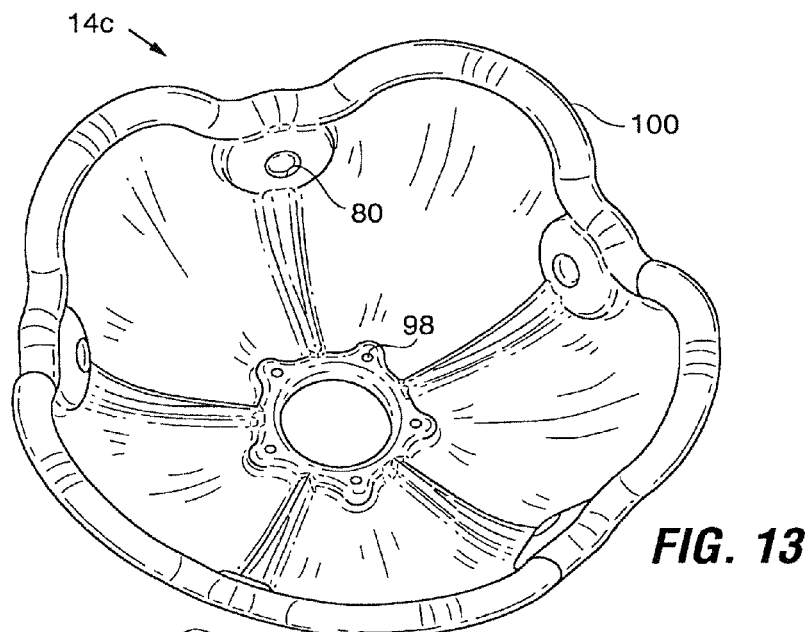
FIG. 13 shows a top perspective view of a fourth embodiment of a restrictor.

Yet another alternative restrictor 14c (FIG. 13) is molded out of highly compliant material (such as 40 shore 00 silicone) to put minimal stress on attached stomach tissue. This embodiment includes a reinforced proximal rim 100.

Figure 14A:
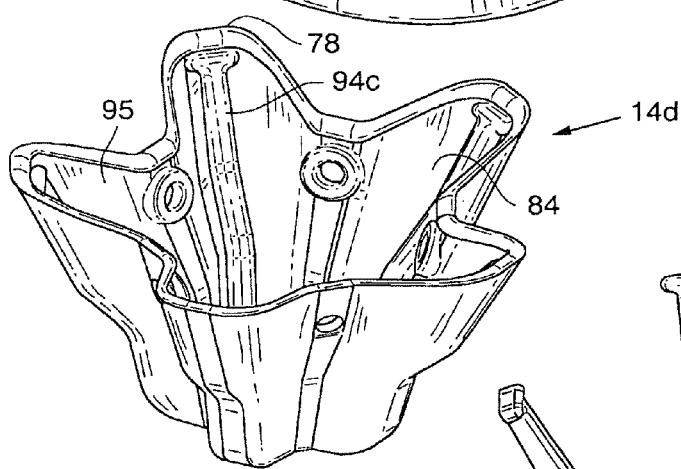
FIG. 14A shows a side perspective view of a fifth embodiment of a restrictor.
Figure 14B:
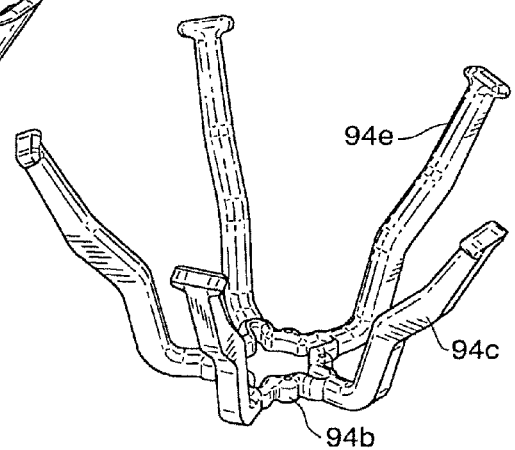
FIG. 14B is a perspective view of the embodiment of FIG. 14A, showing only the rib structure.

An additional restrictor 14d is molded out of a combination of high and low compliance material (such as 50 shore A plus 40 shore 00 silicones) in different areas of the restrictor to achieve optimal performance. A rib structure 94c (see FIG. 14B) out of stiffer material serves to maintain the restrictor shape in the open position within the stomach. IN this example, rib structure 94c includes an undulating ring 94d encircling the orifice 86, and ribs 94e extending to peaks 78. In this manner, the rib structure 94c maintains apposition of the restrictor against the wall of the stomach in order to improve the effectiveness of catching food, particularly in the chutes 84. In addition to the stiffer rib structure, the assembled restrictor contains a very soft web 95 of material that forms the funnel shape and also serves to link together the anchor points 80 (see FIG. 14A). The soft compliant nature of the web material minimizes the stress to the plication tissue by allowing full flexibility.

Restrictor Guide Tool

Restrictor guide 20 generally includes a tubular shaft 101, a distal portion comprising a coupling element/mount 102 and a proximal portion 104.

In a preferred restrictor guide, the mount 102 is designed to support the restrictor 14 during delivery of the restrictor into the stomach and coupling of the restrictor 12 to the stomach wall (directly or using anchors or other means as disclosed herein). In the illustrated embodiment, mount 102 includes a collar 103 on the distal end of the shaft 101. A pair of tubes 112 extend distally between the collar 103 and a ring 107. Ring 107 includes a plurality of distally extending pins 106 and a central opening 109. A tube 111 is positioned co-axially with the opening 109. A distal cap 108 is mounted to the distal end of the tube 111. Cap 108 includes an opening positioned in alignment with the opening of the ring 107 and the lumen of the tube 111. Bores 110 in the cap are positioned so that proximal advancement of the cap 108 relative to the ring 107 causes pins 106 to enter the bores 110.

Figure 17A:
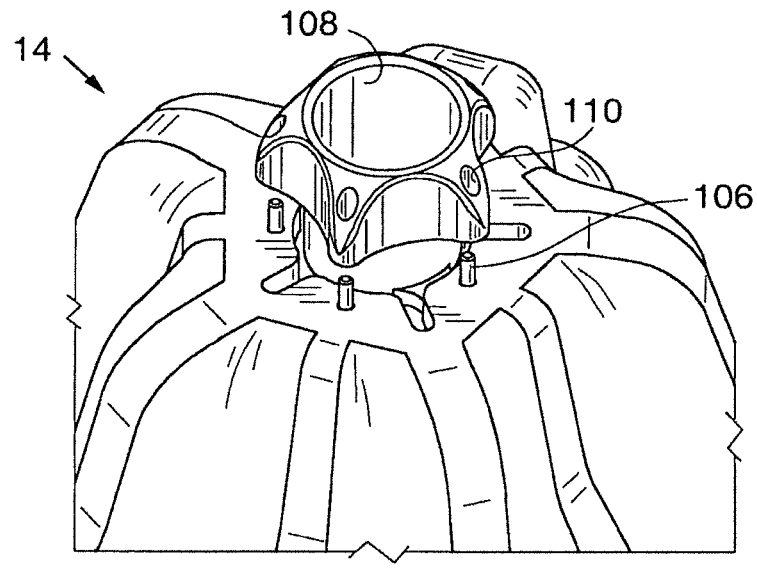
FIG. 17A is a perspective view of a restrictor, showing the restrictor positioned on the restrictor guide, with the mount in the open configuration.
Figure 17B:
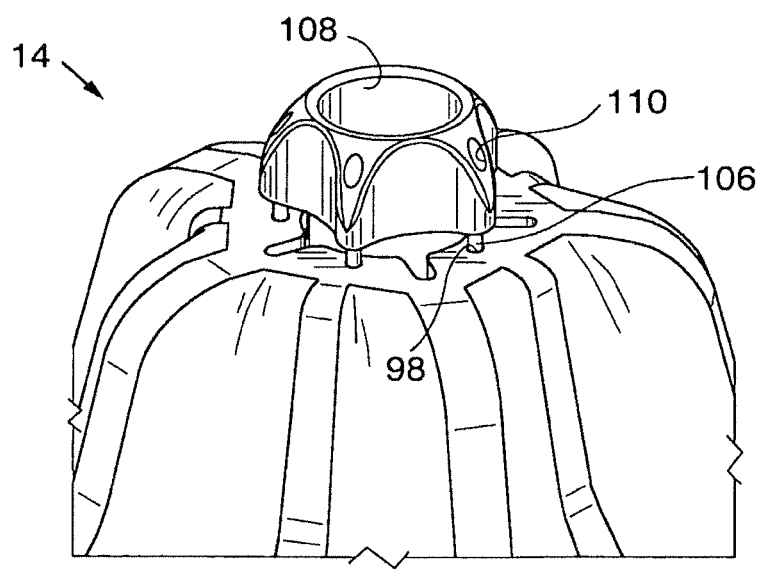
FIG. 17B is similar to FIG. 17A but shows the mount in the closed configuration.
Figure 17C:
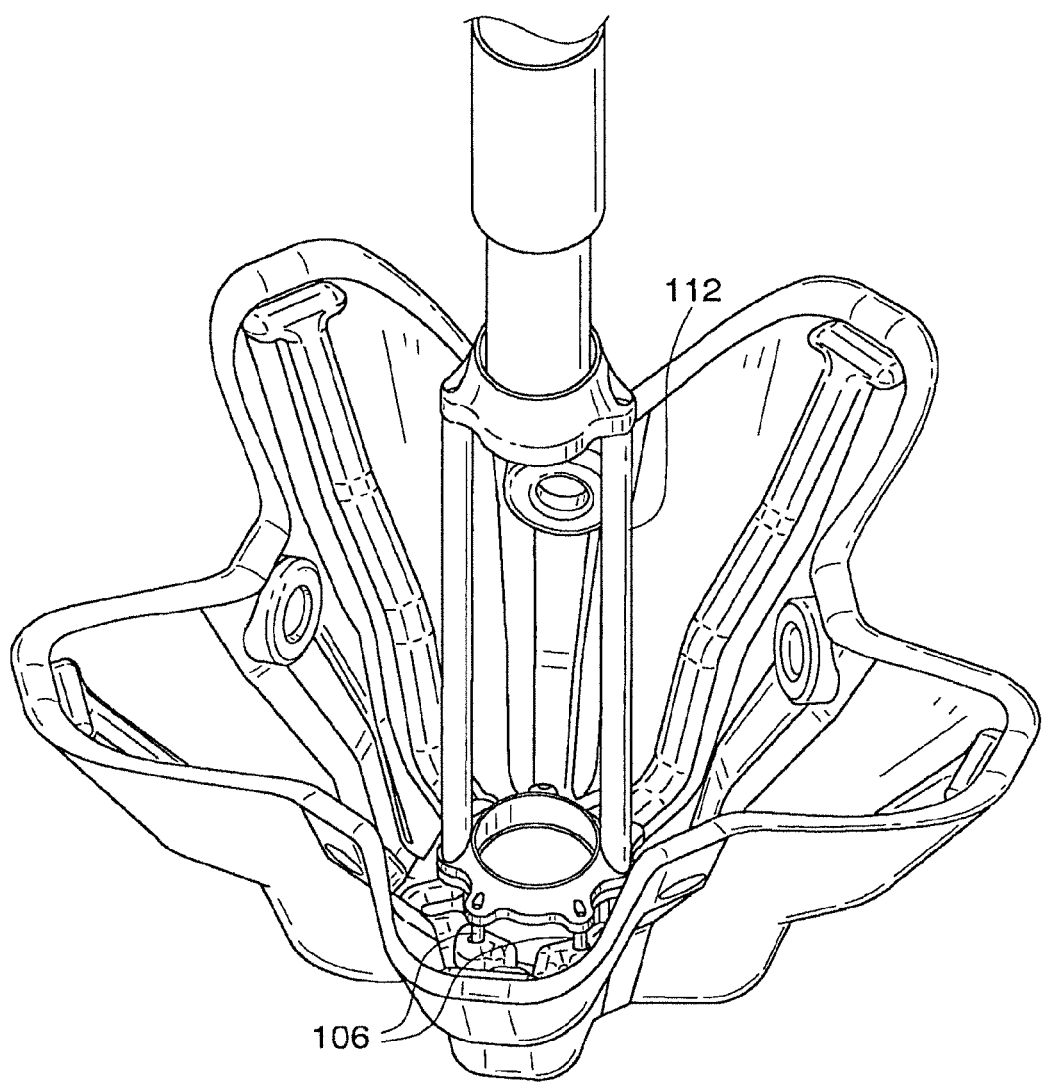
FIG. 17C is a perspective showing the interior of a restrictor positioned on the restrictor guide.

Referring to FIG. 17A, pins 106 are arranged to allow a user to couple the restrictor 14 to the restrictor mount by threading the holes 98 surrounding the orifice in the restrictor 14 over the pins 106 as shown. When the restrictor 14 is mounted in this way, the tube 111 is disposed in the orifice 86 of the restrictor, and the cap 108 is positioned distal to the restrictor. Restrictor 14 is retained on the mount 102 by moving the cap 108 in a proximal direction until bores 110 slide over the pins 106, thus capturing the restrictor 14 between the cap 108 and the ring 107 by preventing the restrictor from sliding off the pins. See FIG. 17B.

Figure 16B:
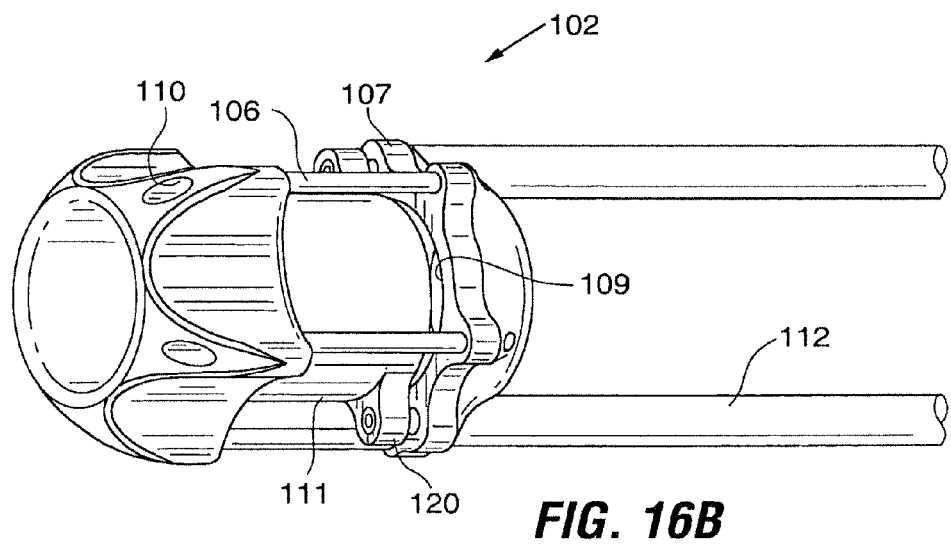
FIG. 16B is similar to FIG. 16A and shows the mount in the closed configuration.
Figure 16C:
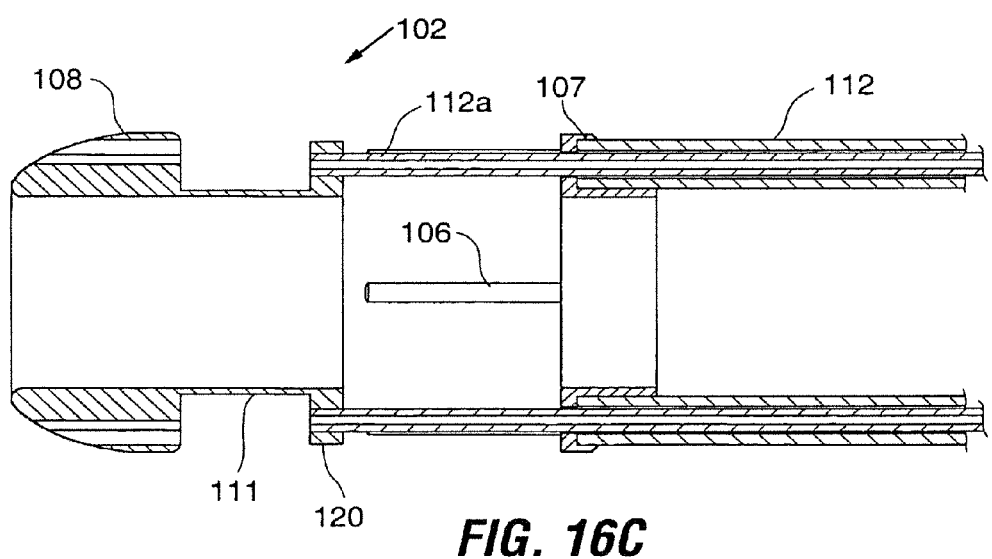
FIG. 16C is a cross-section view of the mount in the open configuration.

Drive rods 112a (FIG. 16A) extend through the tubes 112 and are coupled at their distal ends to flanges 120 on the proximal end of tube 111. The proximal ends of the drive rods 112a are advanceable by an actuator at the proximal end of the restrictor guide. Manipulation of the actuator will cause the drive rods 112a to move distally relative to the tubes 112, causing distal movement of the cap 108 relative to the ring 107. In one current embodiment, rotation of a threaded nut on the proximal handle moves a threaded piece inside the handle that is connected to wires or cables that communicate with the drive rods 112a. In another embodiment, the drive rods 112a may be lead screws, and the actuator may include a knob and associated gearing for rotating the lead screws such that they advance the cap 108 distally. Alternatively, the actuator may include a spring that is initially locked in a compressed position using a latch. According to this embodiment, a button or other element is manipulated by the user to disengage the latch, thus releasing the spring from the compressed position to drive the drive rods distally. Other alternatives include pneumatic or hydraulic actuation of the cap 108. In other embodiments, the actuator may be a handle that allows the user to manually advance the drive rods to advance the cap.

Proximal portion 104 of the restrictor guide 20 is a multi-lumen guide having a central lumen 114 through which the tubular shaft 101 extends, and a plurality of peripheral lumens 116 arranged around the central lumen. The peripheral lumens 116 are proportioned to accommodate the anchor graspers 18. Each of the peripheral lumens 116 has a proximal port fitted with a seal (which may be, for example, a duck bill seal) that will seal around the shaft of a grasper 18 positioned in the lumen, and that will self-seal when the grasper 18 is removed from the lumen.

Exemplary Procedure

Use of the system 10 to implant a restrictor 14 will next be described. According to one embodiment, the method is performed following an initial procedure in which a plurality of plications P having cutouts or other openings C are formed. In another embodiment, after each plication is formed, an anchor 12 is implanted in that plication's opening for the dual purpose of marking the location of the plication as well as ensuring that the opening does not close in the natural healing process of the tissue. The anchor implantation procedure may immediately precede restrictor implantation, or may instead be performed in advance of the restrictor implantation procedure to allow reinforcement of the plications through the body's healing process.

Figure 19A:
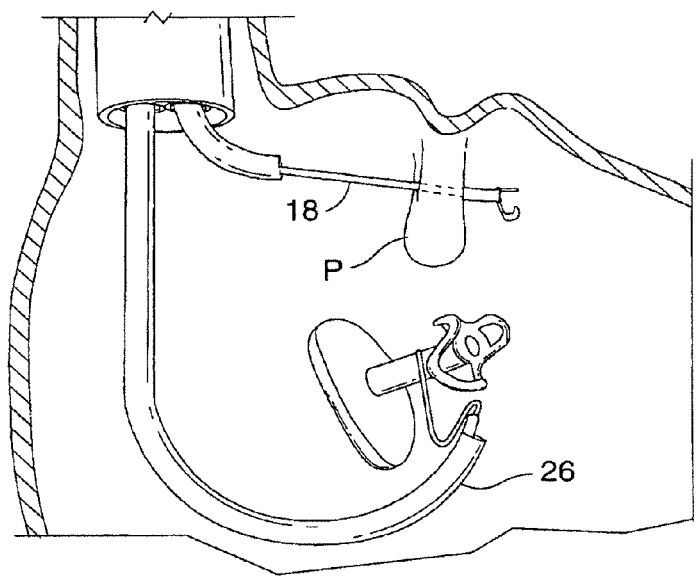
FIGS. 19A and 19B schematically illustrate elements of the system positioned in the stomach in preparation for transferring an anchor from an anchor hand-off to the anchor grasper that will then draw the anchor through the opening in the plication.

In the initial phase of the restrictor implantation procedure, anchors 12 are positioned in the openings of the plications P. Referring to FIG. 19A, the endogastric tube 22 is introduced into the mouth and through the esophagus, and parked with its distal opening in a portion of the stomach or esophagus that is proximal to the plications P. After each plication with opening is created, a multi-lumen (or cannulation) guide tube 24 may be passed through the endogastric tube 22. Multi-lumen guide tube 24 may have a central lumen 24a and peripheral lumen 24b in a similar arrangement to the lumen of the restrictor guide 20 (FIG. 18B).

Figure 19B:
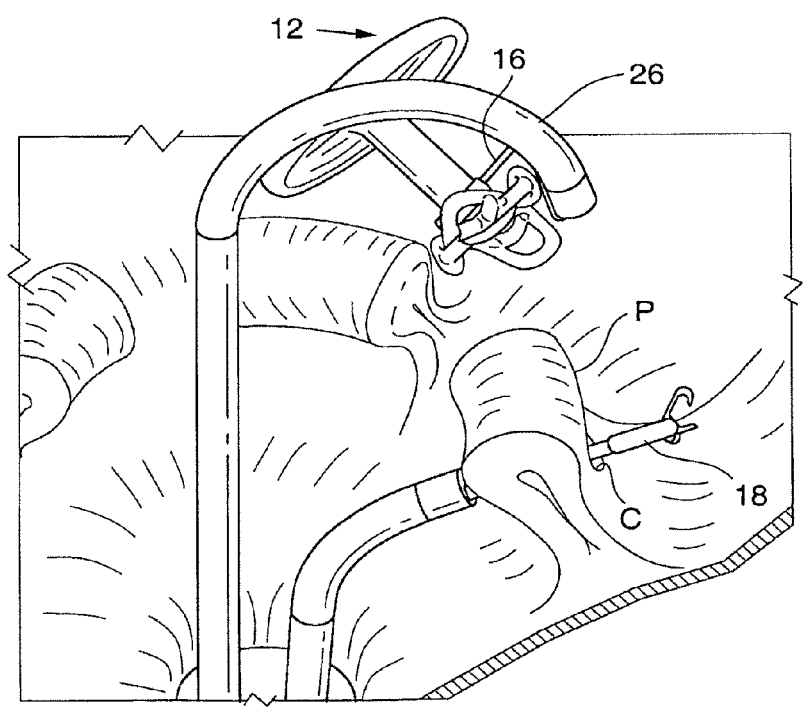

Outside the body, an anchor hand-off 16 is passed through a tool channel of an endoscope 26 such that the anchor engaging wire 48 extends from the endoscope lumen. With the engaging wire in this position, an anchor 12 is coupled to the engaging wire 48, and the endoscope 26, anchor hand-off 16, and anchor 12 are together passed through the central lumen 24a of the multi-lumen guide tube 24 and into the stomach as shown in FIGS. 19A and 19B. The endoscope 26 is retroflexed within the stomach to provide visualization of the plication P.

Next, an articulating guide 25 is advanced through a peripheral lumen 24b of the multi-lumen guide tube 24 and into the stomach. An anchor grasper 18 is positioned in the lumen of the guide 25. Under visualization using endoscope 26 (with anchor hand-off 18 retracted so that the anchor is out of view), guide 25 is articulated to orient the grasper 18 towards the opening C in the plication, and the grasper 18 is then advanced through the opening as also shown in FIGS. 19A and 19B. The grasping element 50 of the grasper 18 is moved into the open position.

Figure 20F:
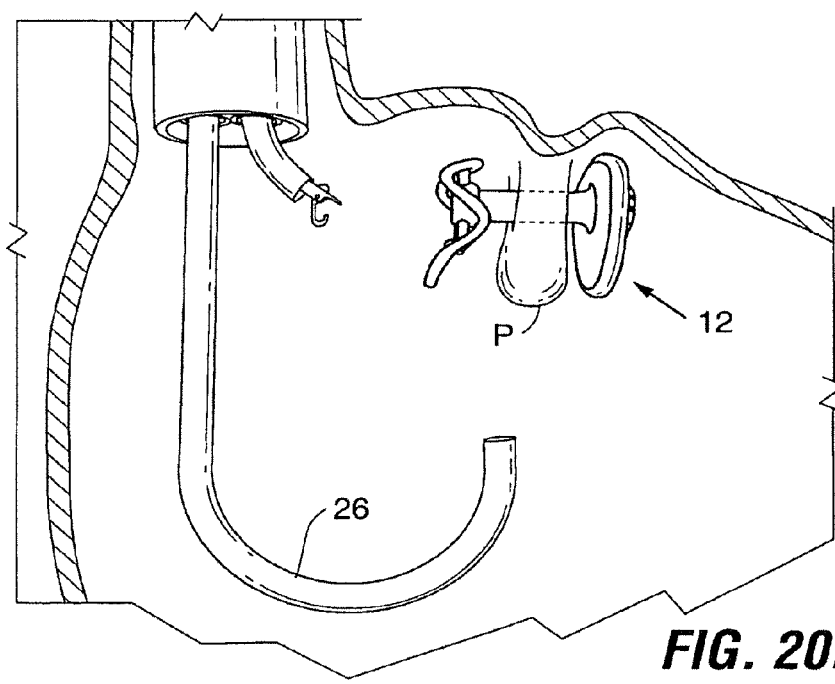
Figure 21A:
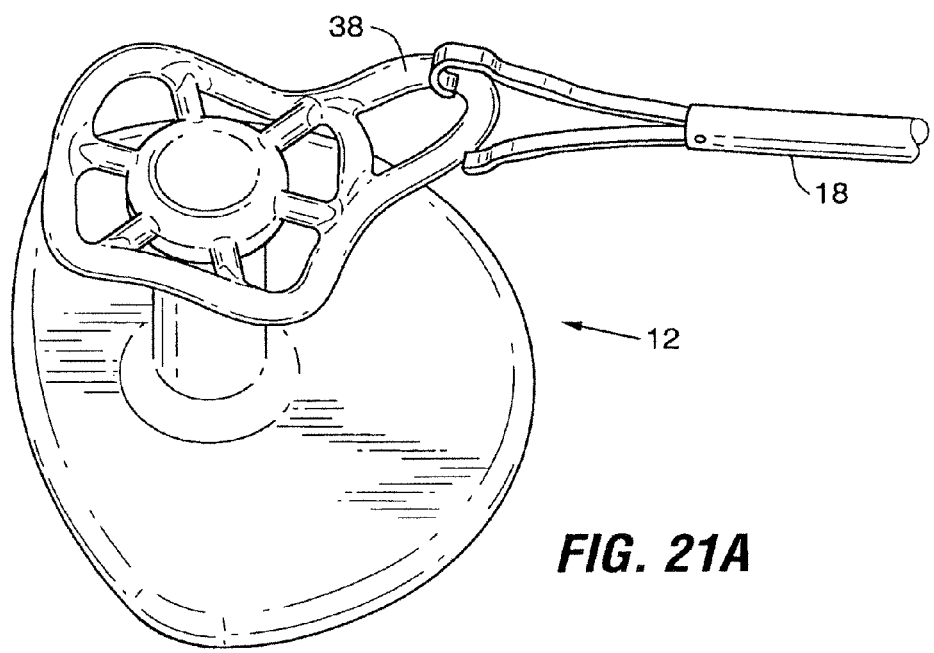
FIGS. 21A and 21B are perspective views showing the anchor grasper engaging different portions of the anchor head.
Figure 21B:
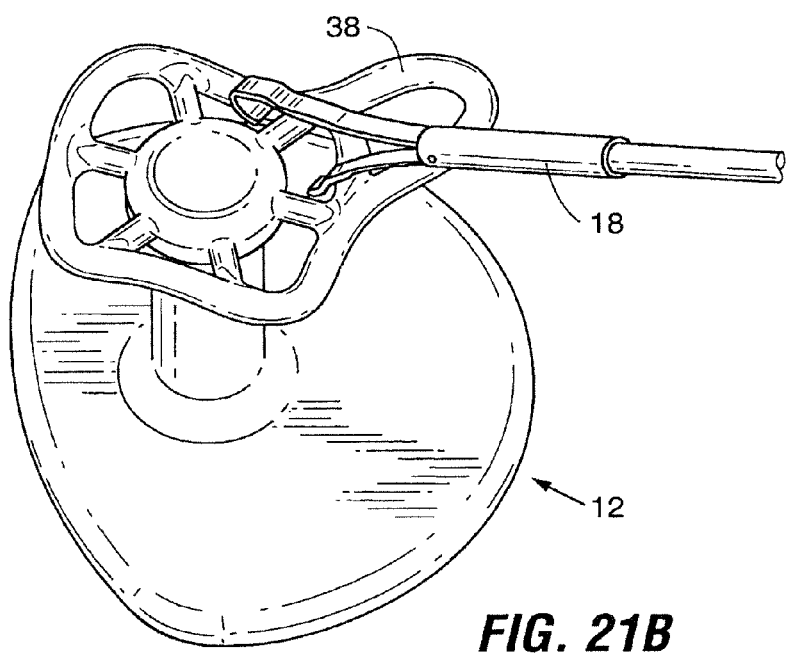

Referring to FIGS, 20A, 20B and 20C, anchor hand-off 16 is advanced further from the endoscope 26 until the head 32 of the anchor is positioned within reach of the grasping element 50. Grasping element 50 is manipulated to engage the head 32. While it is preferable to engage the loop 38 as shown in FIG. 21A, the structure of the head 32 allows for engagement of other portions of the head such as the struts 36 as shown in FIG. 21B, or the ring surrounding the struts 36. Engagement between the anchor and the anchor grasper is secured by moving the grasping element 50 into the locked position. Next, the anchor hand-off is retracted into the endoscope in order to separate it from the anchor grasper. This action results in stretching the anchor stem and thus causing it to release from the horseshoe shaped form. See FIG. 20D. The handle of the anchor grasper 18 is then withdrawn to pull the head 32 of the anchor through the opening C in the plication as in FIG. 20E. As discussed above, application of tension to the head 32 causes the anchor to elongate to a narrow profile that will pass readily through the opening C in the plication. The jaws of the anchor grasper 18 are opened to release the anchor 12. FIG. 20F.

The endoscope 26 and anchor hand-off 16 are withdrawn from the guide tube 24 along with the multiple lumen guide and articulating guide. After another plication is created, the process is repeated for each anchor that is to be implanted. See FIGS. 22A-22C.

Figure 22A:
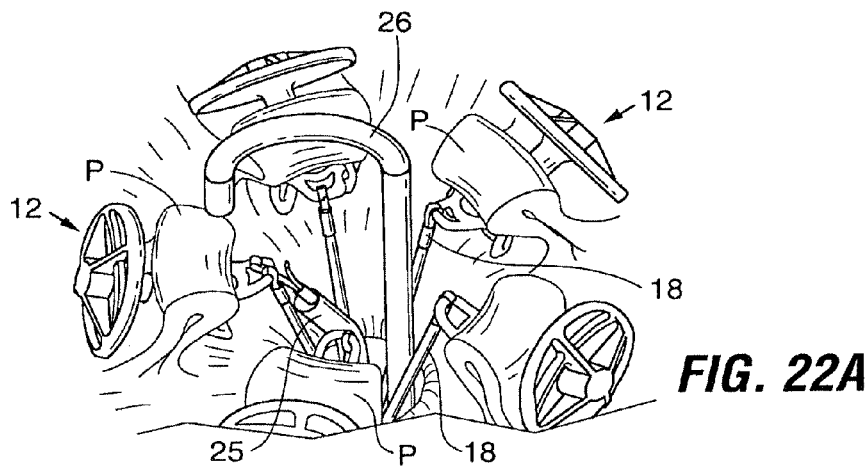
FIGS. 22A, 22B, and 22C schematically illustrate a plurality of anchors that have been placed in plications in the stomach, together with elements of the disclosed system.
Figure 22B:
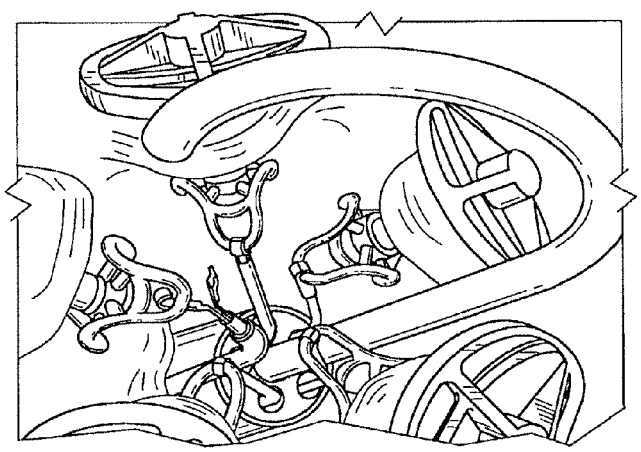
Figure 22C:
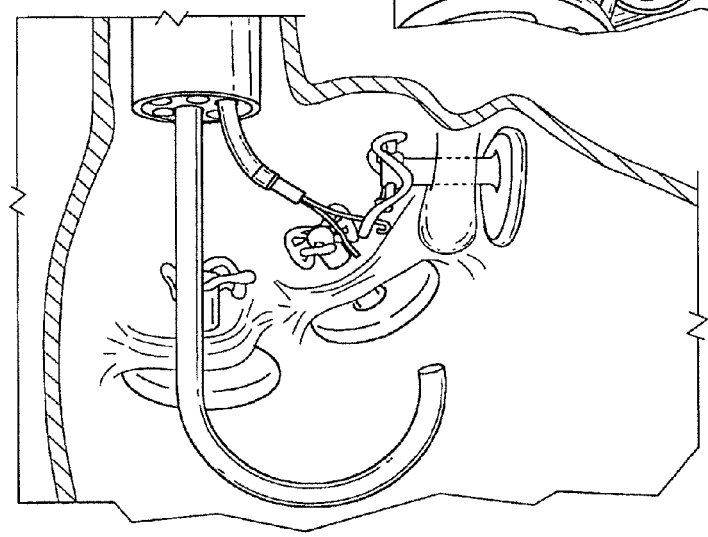

As each anchor is implanted, its corresponding anchor grasper is preferably left coupled to the ring of the anchor, although it may instead be withdrawn from the body. At the end of the anchor-positioning phase of the procedure, each anchor is positioned extending through a plication opening (FIG. 22A). If the anchor graspers were left in place coupled to the rings of each anchor, the handles of each separate anchor grasper 18 extend out of the body. Organization of the anchor graspers 18 is maintained by the multi-lumen cannula 24.

If the anchor graspers 18 are not left in place following implantation of the individual anchors 12, the graspers 18 are re-coupled to the anchors prior to the restrictor-positioning phase. Specifically, each of the graspers 18 is reintroduced into the stomach and endoscopically guided by its corresponding articulated guide 25 into engagement with the head 32 of one of the anchors. As discussed in the Anchors section above, orientation of the loop 38 to extend in a direction opposite to the asymmetrical base 28 helps to orient the loop 38 centrally within the stomach so that the loops 38 may be more easily seen and engaged by the graspers 18.

Figure 23:
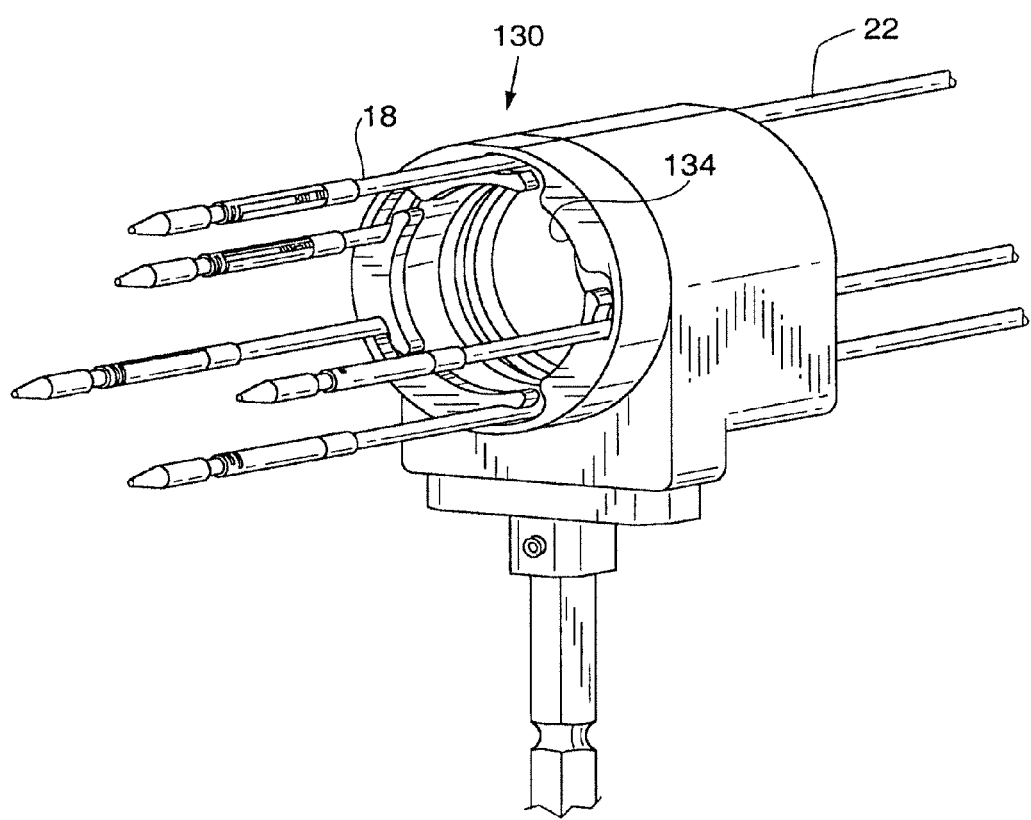
FIG. 23 is a perspective view of the proximal end of the endogastric tube, showing use of the tool organizer.

The restrictor-positioning phase of implantation begins with each anchor that is to be coupled to the restrictor having a separate anchor grasper 18 coupled to it. If the multi-lumen guide 24 is still in use at this point, with individual ones of the graspers 18 in the peripheral lumen 24b, the guide 24 is withdrawn from the endogastric tube 22 and removed from the handles of the anchor graspers. The tapered proximal ends of the anchor graspers 18 allow the lumens 24b of the guide 24 to pass easily over them. Before the multiple lumen guide is completely removed from the endogastric tube 22, the anchor grasper tool shafts are locked into a tool organizer 130 at the proximal end of the endogastric tube 22 as shown in FIG. 23. Organizer 130 includes slots 132 positioned to receive the shafts of the graspers 18, leaving them arranged around the main lumen 134 of the endogastric tube. This serves to maintain the relative clocking of each grasper at the proximal end to a corresponding anchor location at the distal end.

Figure 24A:
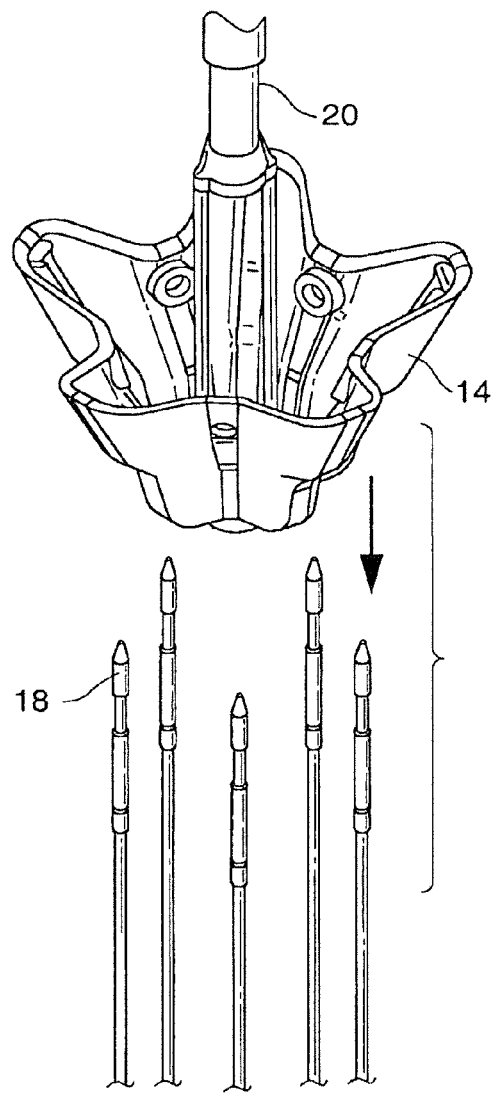
FIG. 24A is a perspective view of a restrictor being advanced onto proximal ends of a collection of anchor graspers.

The restrictor 14 is prepared for implantation by threading anchor openings 80 in the restrictor over the tapered proximal ends of the anchor graspers 18, which at this point are still extending out of the endogastric tube 22. FIG. 24A. The restrictor 14 is mounted to the mount 102 of the restrictor guide 20 in the manner disclosed in the Restrictor Guide section above. This step may be performed before or after the restrictor is threaded over the anchor graspers.

Figure 24B:
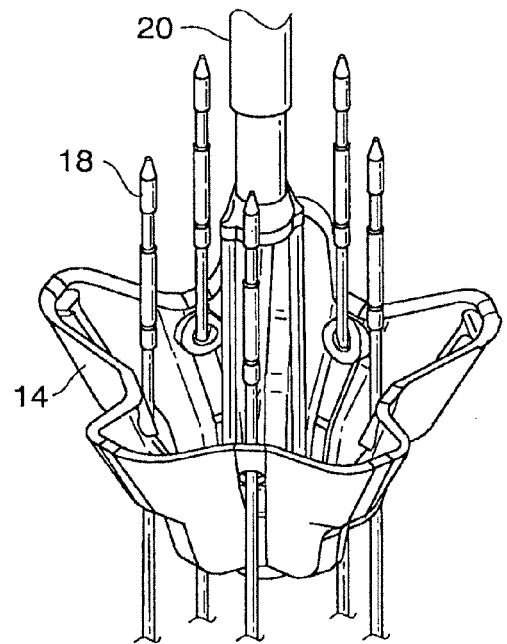
FIG. 24B is a perspective view similar to FIG. 24A showing the restrictor advanced further along the anchor graspers.

Next, the restrictor guide 20 is advanced over the tapered proximal ends of the anchor graspers 18, which are still extending out of the endogastric tube 22. The restrictor guide 20 is positioned so that each of its peripheral lumens 116 advances over a separate one of the anchor graspers 18. FIG. 24B. Continued distal advancement of the guide 20 advances the guide 20 and restrictor 14 through the endogastric tube 22 and into the stomach.

Figure 25A:
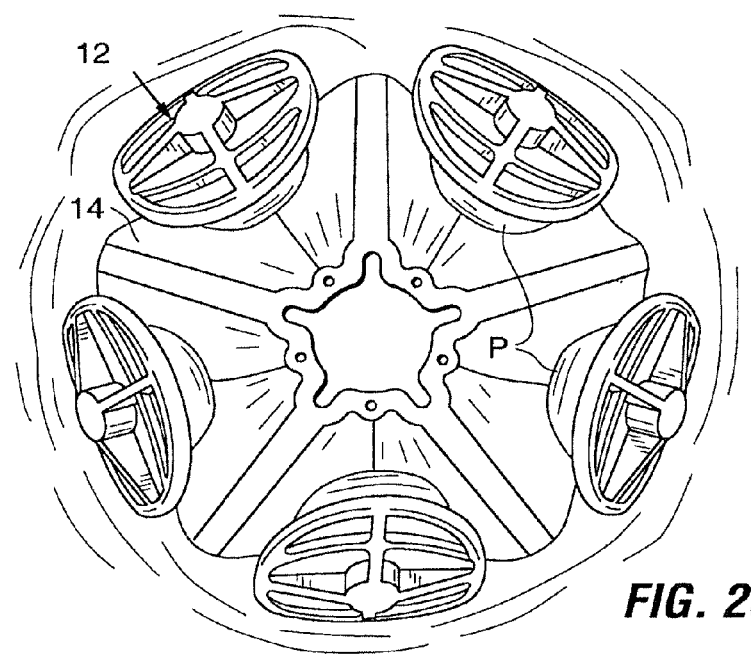
FIG. 25A is a schematic illustration showing the downstream side of a restrictor within the stomach, anchored to plications using anchors.
Figure 25B:
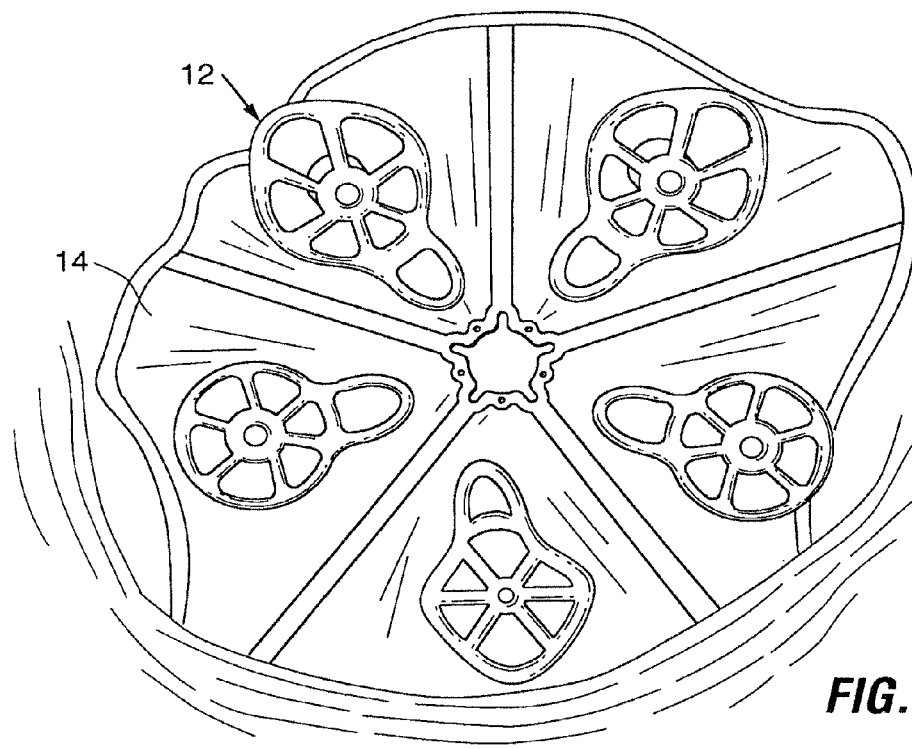
FIG. 25B is a schematic illustration showing the upstream side of a restrictor within the stomach, anchored to plications using anchors.
Figure 26A:
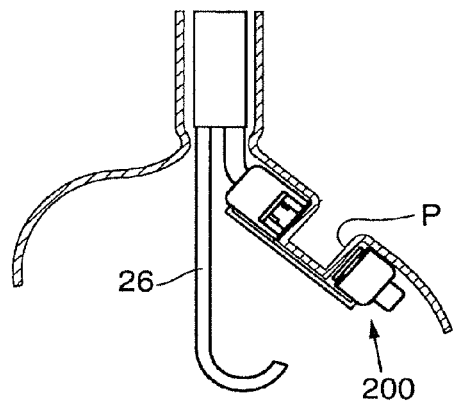
FIGS. 26A, 26B, 26C, and 26D schematically illustrate use of the plicator for forming tissue plications and for forming holes in the plicated tissue.
Figure 26B:
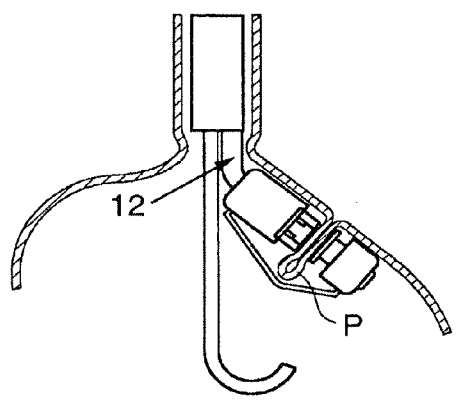
Figure 26C:
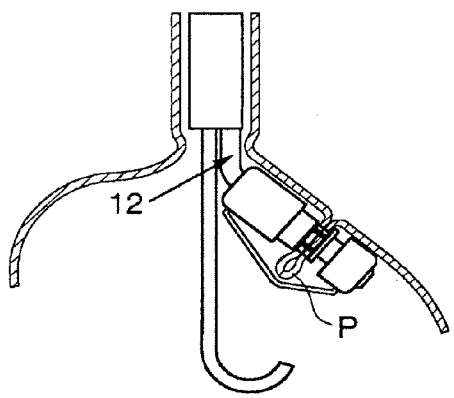
Figure 26D:
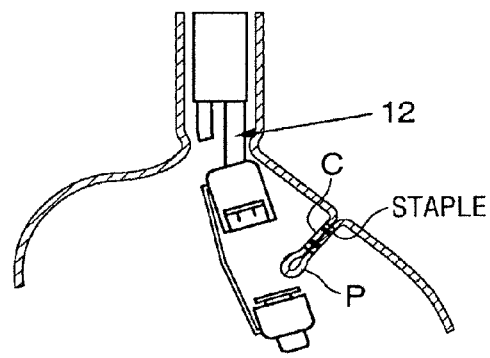

In a final step, the anchors 12 are pulled through the anchor openings 80 to couple the restrictor 14 to the anchors 12. In this step, distally-oriented pressure is applied to the restrictor guide 20 while the anchor graspers 18 are one-by-one pulled proximally, causing the anchors 12 to elongate sufficiently to pass through the openings 90. Coupling between each anchor and its corresponding opening 80 is confirmed visually and/or by tactile feedback reflecting the "pop" of the anchor moving through the opening 80. Once the restrictor 14 has been coupled to the anchors 12, the cap 108 of the restrictor guide 20 is advanced distally to release the restrictor as described in the Restrictor Guide section above. The anchor graspers 18 are unlocked and separated from the anchors. The restrictor guide 20, anchor graspers 18, guides, etc. are withdrawn from the body, leaving the restrictor 14 and anchors 12 in place as shown in FIGS. 25A and 25B.

The system of FIG. 3 may additionally include one or more tools for use in forming plications in the stomach wall tissue and for forming holes in the plicated tissue. Examples of such plicators are found in the following co-pending U.S. patent applications: U.S. Publication No. U.S. 2007/0219571 (entitled ENDOSCOPIC PLICATION DEVICES AND METHOD), filed Oct. 3, 2006, U.S. application Ser.

No. 11/900,757 (entitled ENDOSCOPIC PLICATION DEVICE AND METHOD), filed Sep. 13, 2007, and U.S. application Ser. No. 12/050,169 (entitled ENDOSCOPIC STAPLING DEVICES AND METHODS), filed Mar. 18, 2008.

Use of one such tool is generally illustrated in FIGS. 26A-26D and includes drawing stomach wall tissue into a vacuum chamber of a plication head (FIG. 26A), compressing the tissue (FIG. 26B), advancing fasteners such as staples through the compressed tissue and forming a cut or hole in the compressed tissue (FIG. 26C), and releasing the tissue from the plication tool, leaving the plication with a hole or cut out through the plicated tissue. In one staple arrangement, a pair of annular staple patterns encircle the cut/hole. Anchors can be subsequently positioned within the hole/cutout as disclosed above.

Although the disclosed system has been described in the context of implanting a restrictor implants implantable in the stomach for limiting limit intake of food by the patient, the systems and methods may be used to implant other types of implants for a variety of purposes. These implants include, but are not limited to obstructive gastric implants that obstruct flow of food into the stomach, gastric space occupiers for limiting effective stomach volume, prosthetic valves for the treatment of gastro-esophageal reflux disease, gastric stimulators, pH monitors and drug eluting devices that release drugs, biologics or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g., growth factor, cytokines) which aid in post surgery trauma, ulcers, lacerations, etc. Still other implants might be of a type which might provide a platform to which specific cell types can adhere, grow and provide biologically-active gene products to the GI tract, and/or a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices. Additionally, the disclosed anchors and restrictors are shown positioned and anchored near the gastro-esophageal junction region of the proximal stomach, but may be positioned and/or anchored elsewhere in the stomach or GI system.

It should also be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

Any and all patents and patent applications referred to herein, including for purposes of priority, are incorporated herein by reference It is claimed:

1. A method for implanting an implant in a patient, comprising:
    inserting an implant transorally into the patient and positioning the implant such that food is configured to pass through the implant and into a stomach, wherein the implant includes a proximal opening, a distal opening, and an implant wall between the proximal and distal openings, wherein, prior to the inserting step, a gastro-esophageal junction region of the patient includes a tissue fold and at least one anchor positioned through the tissue fold; and
    deforming a first end of the anchor into an elongated configuration, wherein the first end of the anchor and a second end of the anchor are both larger than a middle portion of the anchor, and pulling the first end of the anchor through the implant wall such that the anchor couples the implant to the tissue fold in the gastro-esophageal junction region.

2. The method of claim 1, wherein the implant includes a plurality of apertures through the wall.

3. The method of claim 1, further comprising forming a plurality of tissue folds in the gastro-esophageal region, wherein the tissue fold is one of the plurality of tissue folds.

4. The method of claim 3, wherein each of the plurality of tissue folds includes an opening, and the method further comprises inserting anchors through each of the openings.

5. The method of claim 1, wherein the method further comprises inserting the anchor through an opening of the tissue fold.

6. The method of claim 1, wherein the distal opening is smaller than the proximal opening.

7. A method for implanting an implant in a patient, comprising:
    inserting an implant transorally into a patient, wherein the implant includes a proximal opening, a distal opening smaller than the proximal opening, a wall connecting the proximal and distal openings, and an aperture through the wall;
    positioning the proximal opening proximate the gastro-esophageal junction and the distal opening in a stomach such that food is configured to pass through the implant and into the stomach; and
    manipulating a first end of an anchor through the aperture by placing a tool through the aperture, and using the tool to deform the first end from an expanded configuration to an elongated configuration, then allowing the first end to transition back to the expanded configuration such that the anchor couples the implant to tissue in the gastro-esophageal junction region, wherein the first end of the anchor and a second end of the anchor are both larger than a middle portion of the anchor.

8. The method of claim 7, wherein the distal opening is normally open.

9. The method of claim 7, wherein the wall of the implant includes a plurality of undulations.

10. The method of claim 7, wherein the implant includes a plurality of apertures proximate the proximal opening.

11. The method of claim 7, further comprising securing the anchor to tissue in the gastro-esophageal junction region.

12. The method of claim 7, further comprising inserting the tool through the proximal opening of the implant.

13. The method of claim 7, wherein the tissue includes a tissue fold, and the anchor passes through the tissue fold.

14. The method of claim 7, further comprising forming a plurality of tissue folds in the gastro-esophageal region, wherein the tissue includes one of the plurality of tissue folds, and the method further comprises coupling the implant to a remaining plurality of tissue folds.

15. The method of claim 14, further comprising coupling the implant to each of the remaining plurality of tissue folds using anchors.

16. The method of claim 15, wherein each of the anchors used to couple the implant to the plurality of tissue folds includes a first end, a second end, and a middle portion, wherein each of the first and second ends is larger than the middle portion.

17. The method of claim 7, wherein the first end of the anchor includes a ring deformable between the expanded configuration and the elongated configuration.

18. A method for implanting an implant in a patient, comprising:
   inserting an implant transorally into the patient, wherein the implant includes a proximal opening, a distal opening, a wall between the proximal and distal openings, and a plurality of apertures through the wall; and
   manipulating a first end of an anchor through the wall such that the anchor couples the implant to a tissue fold in the gastro-esophageal junction region;
   wherein manipulating the first end of the anchor through the wall includes placing a tool through an aperture of the plurality of apertures, and using the tool to draw the first end of the anchor through the wall.

19. The method of claim 18, wherein the tissue fold includes a hole, and the method further comprises inserting the anchor through the hole.

20. The method of claim 18, wherein the first end of the anchor and a second end of the anchor are both larger than a middle portion of the anchor.

\* \* \* \* \*